United States Patent [19]
Taylor

[11] Patent Number: 6,103,479
[45] Date of Patent: Aug. 15, 2000

[54] MINIATURIZED CELL ARRAY METHODS AND APPARATUS FOR CELL-BASED SCREENING

[75] Inventor: D. Lansing Taylor, Pittsburgh, Pa.

[73] Assignee: Cellomics, Inc., Pittsburgh, Pa.

[21] Appl. No.: 08/865,341

[22] Filed: May 29, 1997

Related U.S. Application Data

[63] Continuation-in-part of application No. 08/810,983, Feb. 27, 1997, Pat. No. 5,989,835.
[60] Provisional application No. 60/018,696, May 30, 1996.

[51] Int. Cl.⁷ .................................................. G01N 33/53
[52] U.S. Cl. ............................ 435/7.2; 422/57; 422/60; 422/63; 435/34; 435/287.8; 435/287.9; 436/518; 436/524; 436/527; 427/466; 427/402; 216/2; 216/11
[58] Field of Search .................................. 422/57, 60, 63; 435/7.2, 34, 287.8, 287.9; 436/518, 524, 527; 427/466, 402; 216/2.11

[56] References Cited

U.S. PATENT DOCUMENTS

| | | |
|---|---|---|
| 4,591,570 | 5/1986 | Chang . |
| 4,656,130 | 4/1987 | Shoshan . |
| 4,673,988 | 6/1987 | Jansson et al. . |
| 4,741,043 | 4/1988 | Bacus . |
| 4,906,439 | 3/1990 | Grenner . |
| 5,096,807 | 3/1992 | Leaback . |
| 5,100,777 | 3/1992 | Chang . |
| 5,108,926 | 4/1992 | Klebe . |
| 5,143,854 | 9/1992 | Pirrung et al. . |
| 5,200,051 | 4/1993 | Cozzette et al. . |
| 5,202,227 | 4/1993 | Matsuda et al. . |
| 5,278,063 | 1/1994 | Hubbell et al. . |
| 5,304,487 | 4/1994 | Wilding et al. . |
| 5,313,264 | 5/1994 | Ivarsson et al. . |
| 5,324,591 | 6/1994 | Georger, Jr. et al. . |
| 5,326,691 | 7/1994 | Hozier . |
| 5,355,215 | 10/1994 | Schroeder et al. . |
| 5,384,261 | 1/1995 | Winkler et al. . |
| 5,405,585 | 4/1995 | Coassin . |
| 5,412,087 | 5/1995 | McGall et al. . |
| 5,470,739 | 11/1995 | Akaike et al. . |
| 5,498,392 | 3/1996 | Wilding et al. . |
| 5,500,071 | 3/1996 | Kaltenbach et al. . |
| 5,510,628 | 4/1996 | Georger, Jr. et al. . |
| 5,512,474 | 4/1996 | Clapper et al. . |
| 5,587,128 | 12/1996 | Wilding et al. . |
| 5,637,469 | 6/1997 | Wilding et al. . |

OTHER PUBLICATIONS

Milan Mrksich and George M. Whitesides, "Using Self-Assembled Monolayers to Understand the Interactions of Man-Made Surfaces with Proteins and Cells," Annu. Rev. Biophys. Biomol. Struct., 1996, 25:55–78.

Robert T. Proffitt, James V. Tran and C. Patrick Reynolds, "A Flourescence Digital Image Microscopy System for Quantifying Relative Cell Numbers in Tissue Culture Plates," Cytometry, 1996, 24:204–213.

(List continued on next page.)

*Primary Examiner*—James C. Housel
*Assistant Examiner*—Bao-Thuy L. Nguyen
*Attorney, Agent, or Firm*—McDonnell, Boehnen, Hulbert & Berghoff; David S. Harper

[57] ABSTRACT

The present invention discloses devices and methods of performing high throughput screening of the physiological response of cells to biologically active compounds and methods of combining high-throughput with high-content spatial information at the cellular and subcellular level as well as temporal information about changes in physiological, biochemical and molecular activities. The present invention allows multiple types of cell interactions to be studied simultaneously by combining multicolor luminescence reading, microfluidic delivery, and environmental control of living cells in non-uniform micro-patterned arrays.

5 Claims, 22 Drawing Sheets

(6 of 22 Drawing Sheet(s) Filed in Color)

OTHER PUBLICATIONS

D. Lansing Taylor, Michael Nederlof, Frederick Lanni and Alan S. Waggoner, "The New Vision of Light Microscopy," American Scientist, Jul.–Aug. 1992, vol. 80, 322–335.

Gabriel P. Lopez, Mark W. Albers, Stuart L. Schreiber, Reed Carroll, Ernest Peralta and George M. Whitesides, Convenient Methods for Patterning the Adhesion of Mammalian Cells to Surfaces Using Self–Assembled Monolayers of Alkanethiolates on Gold, J. Am. Chem. Soc., 1993, 115, 5877–5878.

H.M. McConnell, J.C. Owicki, J.W. Parce, D.L. Miller, G.T. Baxter, H.G. Wada, S. Pitchford, The Cytosensor Microphysiometer: Biological Applications of Silicon Technology, Science, vol. 257, Sep. 1992, 1906–1912.

D. Klienfeld, K.H. Kahler and P.E. Hockberger, "Controlled Outgrowth of Dissociated Neurons on Paterned Substrates," The Journal of Neuroscience, Nov. 1988, 8(11):4098–4120.

Rahul Singhvi, Amit Kumar, gabriel P. Lopez, Gregory N. Stephanopoulos, Daniel I.C. Wang, George M. Whitesides and Donald E. Ingber, "Engineering Cell Shape and Function," Science, vol. 264, Apr. 29, 1994, 696–698.

David A. Stenger, Jacque H. Georger, Charles S. Dulcey, James J. Hickman, Alan S. Rudolph, Thor B. Nielsen, Stephen M. McCort, and Jeffrey M. Calvert, "Coplanar Molecular Assemblies of Amino and Perfluorinated Alkylsilanes: Characterization and Geometric Definition of Mammalian Cell Adhesion and Growth," J. Am. Chem. Soc., 1992, 114, 8435–8442.

Robert T. profitt, James V. Tran and Patrick Reynolds, "Fluorescence Digital Image Microscopy System for Quantifying Relative Cell Number in Tissue Culture Plates," Cytometry, 1996, 24:204–213.

Kevin L. Prime and George M. Whitesides, "Self–Assembled Organic Monolayers: Model Systems for Studying Adsorption of Proteins at Surfaces," Scicense, vol. 252, May 1991, 1164–1167.

Figure 1
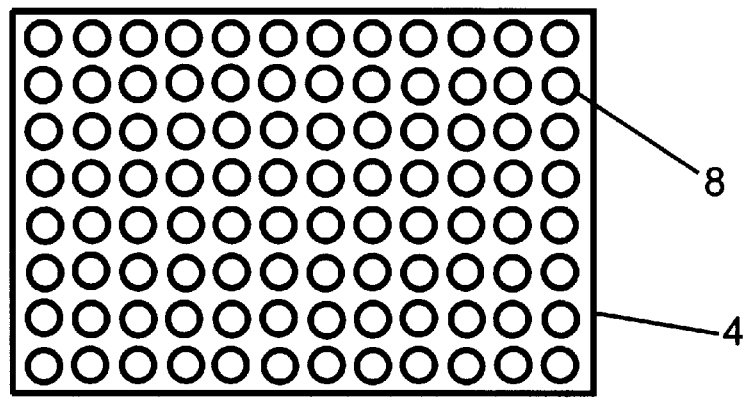
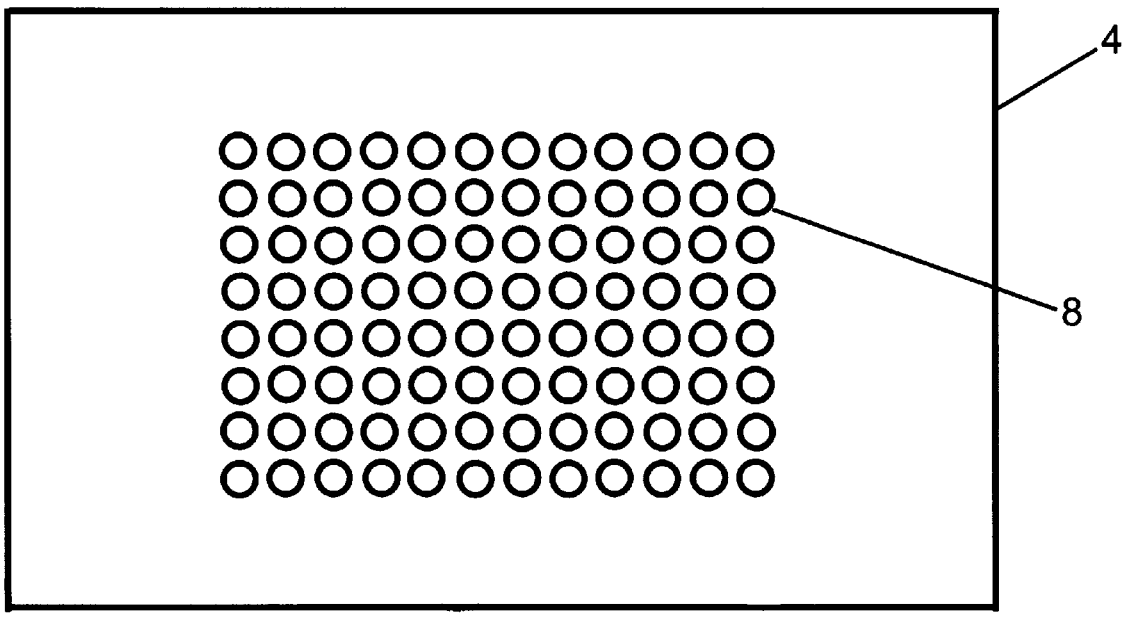

Figure 3B

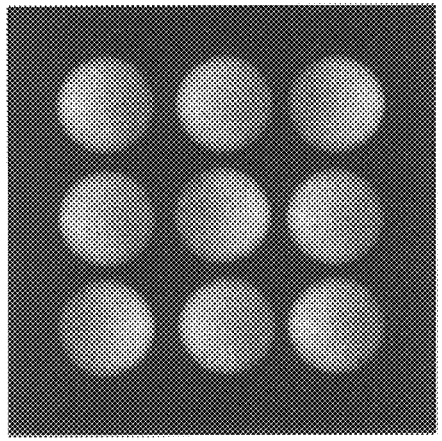

Sodium Fluorescein binding to Cell Chip to identify the location of 200 um spot patterns.

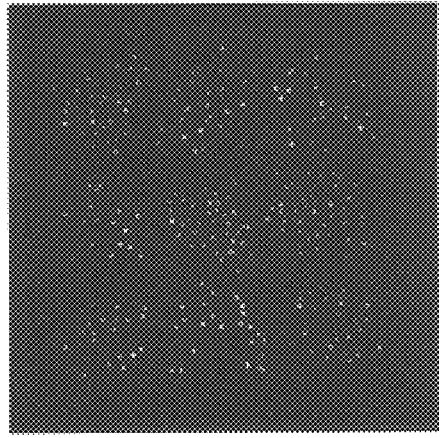

Fluorescent cell attachment of L929 cells to patterned spots (low magnification, 4x)

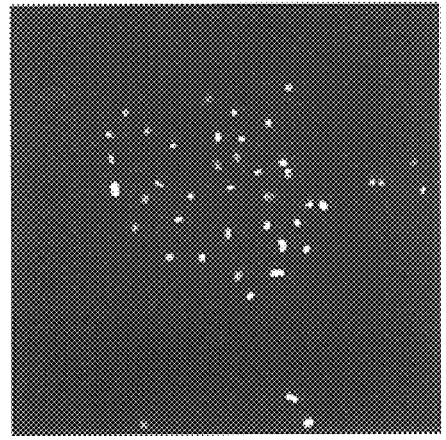

Fluorescent cell attachment of 3T3 cells to patterned spots. Nuclei (above), Actin in same cells (below) (higher magnification, 20x)

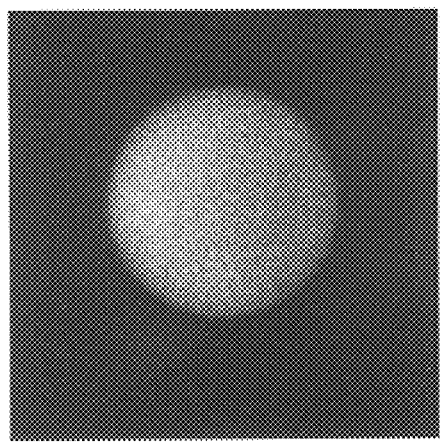

Sodium Fluorescein binding to Cell chip to identify the location of 400 um spots patterns.

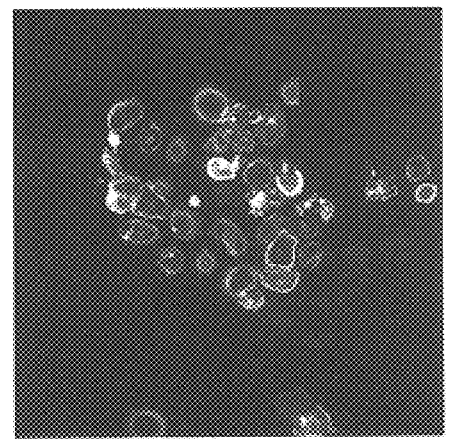

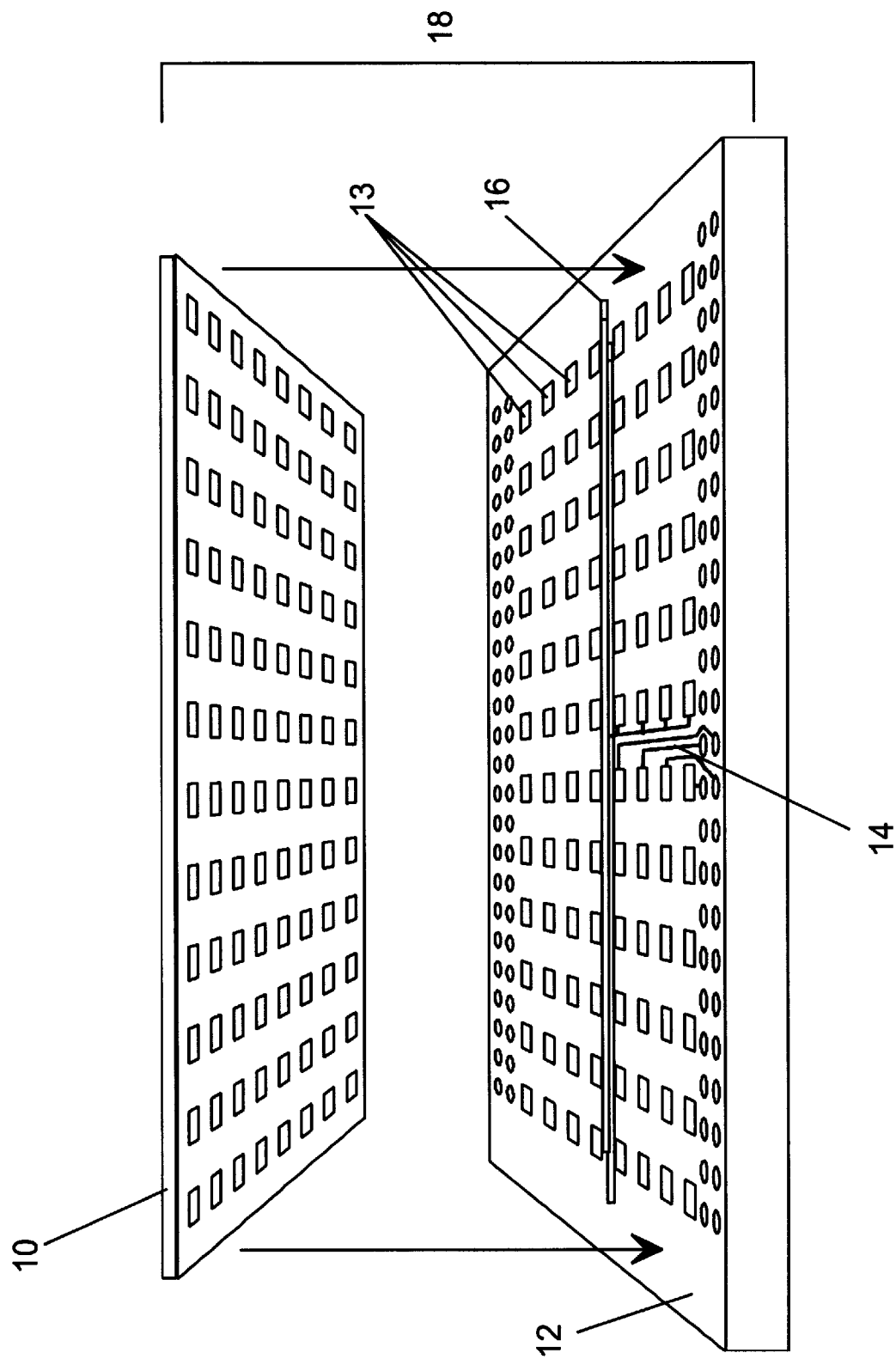

Figure 18
A
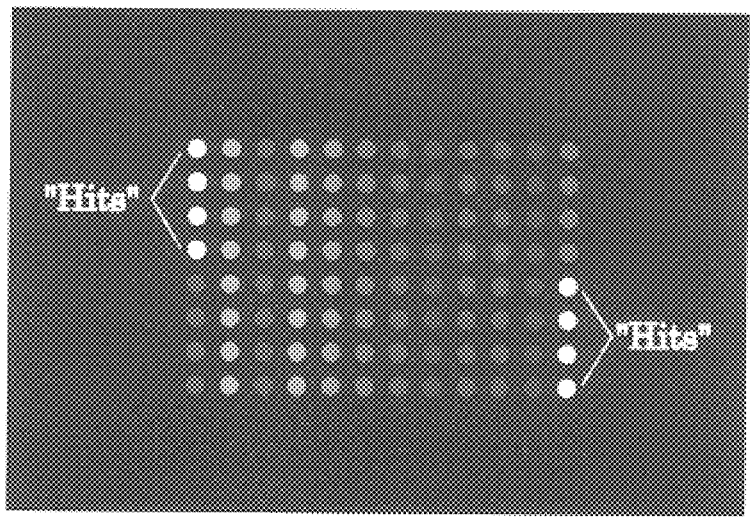
B
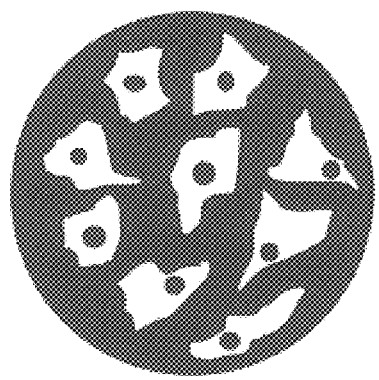 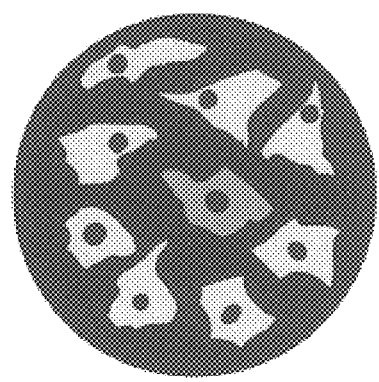
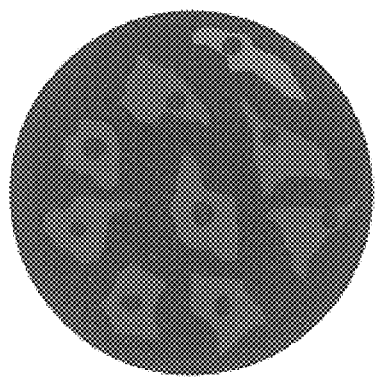 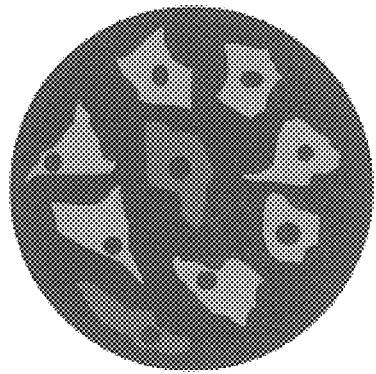

MINIATURIZED CELL ARRAY METHODS AND APPARATUS FOR CELL-BASED SCREENING

RELATED APPLICATIONS

This application is a continuation-in-part of U.S. Provisional Application for patent Ser. No. 60/018,696, filed May 30, 1996, and U.S. application for patent Ser. No. 08/810,983, filed on Feb. 27, 1997, now U.S. Pat. No. 5,989,835 which are both hereby incorporated by reference in their entirety.

FIELD OF THE INVENTION

The present invention relates to methods and apparatus for high throughput and high biological content screening of a non-uniform micro-patterned array of cells on a base.

DESCRIPTION OF THE PRIOR ART

In the expanding arena of drug discovery and combinatorial chemistry to generate candidate compounds, it would be very useful to be able to rapidly screen a large number of substances, via a high throughput screen, for their physiological impact on animals and humans. Before testing the efficacy of a "partially qualified" drug candidate on animals, the drug could first be screened for its biological activity and potential toxicity with living cells prior to testing in an animal model. The anticipated physiological response to the drug candidate could then be based on the results of these cell screens.

Traditionally, "lead compounds" have moved quickly to extensive animal studies which are both time-consuming and costly. Furthermore, extensive drug testing in animals is becoming less and less culturally acceptable in the United States and Europe. Screening drug candidates according to their interaction with living cells, prior to animal studies, can reduce the number of animals required in subsequent drug screening processes by eliminating some drug candidates before going to animal trials. However, manipulation and analysis of drug-cell interactions using current methods does not allow for both high throughput and high biological content screening, due to the small number of cells and compounds that can be analyzed in a given period of time, the cumbersome methods required for compound delivery, and the large volumes of compounds required for testing.

High throughput screening of nucleic acids and polypeptides has been achieved through a technique known as combinatorial chemistry. In typical combinatorial chemistry methods, DNA sequences of 10 to 14 base pairs are attached in defined locations (or spots), up to tens of thousands in number, on a small glass plate. (U.S. Pat. No. 5,556,752, hereby incorporated by reference). This creates an array of spots of DNA on a given glass plate. The location of a spot in the array provides an address for later reference to each spot of DNA. The DNA sequences are then hybridized with complementary DNA sequences labeled with fluorescent molecules. Signals from each address on the array are detected when the fluorescent molecules attached to the hybridizing nucleic acid sequences fluoresce in the presence of light. Such glass plates having an array of nucleic acid sequences affixed thereto are available under the trade name "GENECHIP™" from Affymetrix. These devices have been used to provide high throughput screening of DNA sequences in drug discovery efforts and in the human genome sequencing project. Similarly, protein sequences of varying amino acid lengths have been attached in discrete spots as an array on a glass plate. (U.S. Pat. No. 5,143,854, incorporated by reference herein).

The information provided by an array of either nucleic acids or amino acids bound to glass plates is limited according to their underlying "languages". For example, DNA sequences have a language of only four nucleic acids and proteins have a language of about 20 amino acids. In contrast, a living cell which comprises a complex organization of biological components has a vast "language" with a concomitant multitude of potential interactions with a variety of substances, for example DNA, RNA, cell surface proteins, intracellular proteins and the like. Because a typical target for drug action is with and within the cells of the body, cells themselves can provide a useful screening tool in drug discovery when combined with sensitive detection reagents. It thus would be most useful to have a high throughput, high content screening device to provide high content spatial information at the cellular and subcellular level as well as temporal information about changes in physiological, biochemical and molecular activities (U.S. application Ser. No. 08/810983).

Microarrays of Cells

Methods have been described for making uniform micropatterned arrays of cells for other applications, for example photochemical resist-photolithograpy. (Mrksich and Whitesides, Ann. Rev. Biophys. Biomol. Struct. 25:55–78, 1996). According to this photoresist method, a glass plate is uniformly coated with a photoresist and a photo mask is placed over the photoresist coating to define the "array" or pattern desired. Upon exposure to light, the photoresist in the unmasked areas is removed. The entire photolithographically defined surface is uniformly coated with a hydrophobic substance such as an organosilane that binds both to the areas of exposed glass and the areas covered with the photoresist. The photoresist is then stripped from the glass surface, exposing an array of spots of exposed glass. The glass plate then is washed with an organosilane having terminal hydrophilic groups or chemically reactable groups such as amino groups. The hydrophobic organosilane binds to the spots of exposed glass with the resulting glass plate having an array of hydrophilic or reactable spots (located in the areas of the original photoresist) across a hydrophobic surface. The array of spots of hydrophilic groups provides a substrate for non-specific and non-covalent binding of certain cells, including those of neuronal origin (Kleinfeld et al., J. Neurosci. 8:4098–4120, 1988). Reactive ion etching has been similarly used on the surface of silicon wafers to produce surfaces patterned with two different types of texture (Craighead et al., Appl. Phys. Lett. 37:653, 1980; Craighead et al., J. Vac. Sci. Technol. 20:316, 1982; Suh et al. Proc. SPIE 382:199, 1983).

In another method based on specific yet non-covalent interactions, photoresist stamping is used to produce a gold surface coated with protein adsorptive alkanethiol. (Singhvi et al., Science 264:696–698, 1994). The bare gold surface is then coated with polyethylene-terminated alkanethiols that resist protein adsorption. After exposure of the entire surface to laminin, a cell-binding protein found in the extracellular matrix, living hepatocytes attach uniformly to, and grow upon, the laminin coated islands (Singhvi et al. 1994). An elaboration involving strong, but non-covalent, metal chelation has been used to coat gold surfaces with patterns of specific proteins (Sigal et al., Anal. Chem. 68:490–497, 1996). In this case, the gold surface is patterned with alkanethiols terminated with nitriloacetic acid. Bare regions of gold are coated with tri(ethyleneglycol) to reduce protein adsorption. After adding $Ni^{2+}$, the specific adsorption of five histidine-tagged proteins is found to be kinetically stable.

More specific uniform cell-binding can be achieved by chemically crosslinking specific molecules, such as proteins, to reactable sites on the patterned substrate. (Aplin and Hughes, Analyt. Biochem. 113:144–148, 1981). Another elaboration of substrate patterning optically creates an array of reactable spots. A glass plate is washed with an organosilane that chemisorbs to the glass to coat the glass. The organosilane coating is irradiated by deep UV light through an optical mask that defines a pattern of an array. The irradiation cleaves the Si—C bond to form a reactive Si radical. Reaction with water causes the Si radicals to form polar silanol groups. The polar silanol groups constitute spots on the array and are further modified to couple other reactable molecules to the spots, as disclosed in U.S. Pat. No. 5,324,591, incorporated by reference herein. For example, a silane containing a biologically functional group such as a free amino moiety can be reacted with the silanol groups. The free amino groups can then be used as sites of covalent attachment for biomolecules such as proteins, nucleic acids, carbohydrates, and lipids. The non-patterned covalent attachment of a lectin, known to interact with the surface of cells, to a glass substrate through reactive amino groups has been demonstrated (Aplin & Hughes, 1981). The optical method of forming a uniform array of cells on a support requires fewer steps and is faster than the photoresist method, (i.e., only two steps), but it requires the use of high intensity ultraviolet light from an expensive light source.

In all of these methods the resulting array of cells is uniform, since the biochemically specific molecules are bound to the micro-patterned chemical array uniformly. In the photoresist method, cells bind to the array of hydrophilic spots and/or specific molecules attached to the spots which, in turn, bind cells. Thus cells bind to all spots in the array in the same manner. In the optical method, cells bind to the array of spots of free amino groups by adhesion. There is little or no differentiation between the spots of free amino groups. Again, cells adhere to all spots in the same manner, and thus only a single type of cell interaction can be studied with these cell arrays because each spot on the array is essentially the same as another. Such cell arrays are inflexible in their utility as tools for studying a specific variety of cells in a single sample or a specific variety of cell interactions. Thus, a need exists for non-uniform micro-patterned cell arrays, in order to increase the number of cell types and specific cell interactions that can be analyzed simultaneously, as well as methods of producing non-uniform micro-patterned cell arrays, in order to provide for high throughput and high biological content screening of cells.

Microfluidics

Efficient delivery of solutions to an array of cells attached to a solid substrate, is facilitated by a system of microfluidics. Methods and apparatus have been described for the precise handling of small liquid samples for ink delivery (U.S. Pat. No. 5,233,369; U.S. Pat. No. 5,486,855; U.S. Pat. No. 5,502,467; all incorporated by reference herein), biosample aspiration (U.S. Pat. No. 4,982,739, incorporated by reference herein), reagent storage and delivery (U.S. Pat. No. 5,031,797 incorporated by reference herein), and partitioned microelectronic and fluidic device array for clinical diagnostics and chemical synthesis (U.S. Pat. No. 5,585,069 incorporated by reference herein). In addition, methods and apparatus have been described for the formation of microchannels in solid substrates that can be used to direct small liquid samples along the surface (U.S. Pat. No. 5,571,410; U.S. Pat. No. 5,500,071; U.S. Pat. No. 4,344,816, all incorporated by reference herein). However, there is no known method for delivering solutions to living cells micro-patterned into non-uniform arrays on solid substrates in a closed optical chamber.

Optical Reading of Cell Physiology

Performing a high throughput screen on many thousands of compounds requires parallel handling and processing of many compounds and assay component reagents. Standard high throughput screens use homogeneous mixtures of compounds and biological reagents along with some indicator compound, loaded into arrays of wells in standard microtiter plates with 96 or 384 wells. (Kahl et al., J. Biomol. Scr. 2:33–40, 1997). The signal measured from each well, either fluorescence emission, optical density, or radioactivity, integrates the signal from all the material in the well giving an overall population average of all the molecules in the well. This type of assay is commonly referred to as a homogeneous assay.

Science Applications International Corporation (SAIC) 130 Fifth Avenue, Seattle, Wash. 98109 describes an imaging plate reader, (U.S. Pat. No. 5,581,487, herein incorporated by reference). This system uses a CCD detector (charge-coupled optical detector) to image the whole area of a 96 well plate. The image is analyzed to calculate the total fluorescence per well for homogeneous assays.

Molecular Devices, Inc. describes a system (FLIPR™) which uses low angle laser scanning illumination and a mask to selectively excite fluorescence within approximately 200 microns of the bottoms of the wells in standard 96 well plates in order to reduce background when imaging cell monolayers. (Schroeder and Neagle, J. Biomol. Scr. 1:75–80, 1996). This system uses a CCD camera to image the whole area of the plate bottom. Although this system measures signals originating from a cell monolayer at the bottom of the well, the signal measured is averaged over the area of the well and is therefore still considered a homogeneous measurement, since it is an average response of a population of cells. The image is analyzed to calculate the total fluorescence per well for cell-based homogeneous assays.

Proffitt et. al. (Cytometry 24:204–213, 1996) describes a semi-automated fluorescence digital imaging system for quantifying relative cell numbers in situ, where the cells have been pretreated with fluorescein diacetate (FDA). The system utilizes a variety of tissue culture plate formats, particularly 96-well microtiter plates. The system consists of an epifluorescence inverted microscope with a motorized stage, video camera, image intensifier, and a microcomputer with a PC-Vision digitizer. Turbo Pascal software controls the stage and scans the plate taking multiple images per well. The software calculates total fluorescence per well, provides for daily calibration, and configures for a variety of tissue culture plate formats. Thresholding of digital images and reagents that fluoresce only when taken up by living cells are used to reduce background fluorescence without removing excess fluorescent reagent.

A variety of methods have been developed to image fluorescent cells with a microscope and extract information about the spatial distribution and temporal changes occurring in these cells. A recent article describes many of these methods and their applications (Taylor et al., Am. Scientist 80:322–335, 1992). These methods have been designed and optimized for the preparation of small numbers of specimens for high spatial and temporal resolution imaging measurements of distribution, amount and biochemical environment of the fluorescent reporter molecules in the cells.

Treating cells with dyes and fluorescent reagents and imaging the cells (Wang et al., In Methods in Cell Biology, New York, Alan R. Liss, 29:1–12, 1989), and genetic engineering of cells to produce fluorescent proteins, such as modified green fluorescent protein (GFP) as a reporter molecule are useful detection methods. The green fluorescent protein (GFP) of the jellyfish *Aequorea Victoria* has an excitation maximum at 395 nm, an emission maximum at 510 nm and does not require an exogenous factor. Uses of GFP for the study of gene expression and protein localization are discussed in Chalfie et al., Science 263:802–805, 1994. Some properties of wild-type GFP are disclosed by Morise et al. (Biochemistry 13:2656–2662, 1974), and Ward et al. (Photochem. Photobiol. 31:611–615, 1980). An article by Rizzuto et al. (Nature 358:325–327, 1992) discusses the use of wild-type GFP as a tool for visualizing subcellular organelles in cells. Kaether and Gerdes (FEBS Letters 369:267–271, 1995) report the visualization of protein transport along the secretory pathway using wild-type GFP. The expression of GFP in plant cells is discussed by Hu and Cheng (FEBS Letters 369:331–334, 1995), while GFP expression in Drosophila embryos is described by Davis et al. (Dev. Biology 170:726–729, 1995). U.S. Pat. No. 5,491,084, incorporated by reference herein, discloses expression of GFP from *Aequorea Victoria* in cells as a reporter molecule fused to another protein of interest. PCT/DK96/00052, incorporated by reference herein, relates to methods of detecting biologically active substances affecting intracellular processes by utilizing a GFP construct having a protein kinase activation site. Numerous references are related to GFP proteins in biological systems. For example, PCT/US95/10165 incorporated by reference herein, describes a system for isolating cells of interest utilizing the expression of a GFP like protein. PCT/GB96/00481 incorporated by reference herein, describes the expression of GFP in plants. PCT/US95/01425 incorporated by reference herein, describes modified GFP protein expressed in transformed organisms to detect mutagenesis. Mutants of GFP have been prepared and used in several biological systems. (Hasselhoff et al., Proc. Natl. Acad. Sci. 94:2122–2127, 1997; Brejc et al., Proc. Natl. Acad Sci. 94:2306–2311, 1997; Cheng et al., Nature Biotech. 14:606–609, 1996; Heim and Tsien, Curr. Biol. 6:178–192, 1996; Ehrig et al., FEBS Letters 367:163–166, 1995). Methods describing assays and compositions for detecting and evaluating the intracellular transduction of an extracellular signal using recombinant cells that express cell surface receptors and contain reporter gene constructs that include transcriptional regulatory elements that are responsive to the activity of cell surface receptors are disclosed in U.S. Pat. No. 5,436,128 and U.S. Pat. No. 5,401,629, both of which are incorporated by reference herein.

The ArrayScan™ System, as developed by BioDx, Inc. (U.S. application Ser. No. 08/810983) is an optical system for determining the distribution, environment, or activity of luminescently labeled reporter molecules in cells for the purpose of screening large numbers of compounds for specific biological activity. The ArrayScan™ System involves providing cells containing luminescent reporter molecules in a uniform array of locations and scanning numerous cells in each location with a fluorescence microscope, converting the optical information into digital data, and utilizing the digital data to determine the distribution, environment or activity of the luminescently labeled reporter molecules in the cells. The uniform array of locations used presently are the industry standard 96 well or 384 well microtiter plates. The ArrayScan™ System includes apparatus and computerized method for processing, displaying and storing the data, thus augmenting drug discovery by providing high content cell-based screening in a large microtiter plate format.

The present invention provides for methods and apparatus which combine multicolor luminescence reading, microfluidic delivery, and environmental control of living cells in non-uniform micro-patterned arrays. Typically, the standard microtiter plate format, the 96 well microtiter plate, has 6 mm diameter wells on a 9 mm pitch. Higher density plates, such as 384 well plates, reduce both the well size and well pitch (for example to 3 mm and 4.5 mm), packing more wells in the same format. The present invention provides for both high throughput and high-content, cell-based assays that typically require an area equivalent to a well size of only 0.2–1.0 mm diameter. Reducing the well size and the array size not only improves the speed and efficiency of scanning for high-content screening, but also allows high throughput screening to be carried out on the same cell array by reading the whole area of the array at lower spatial resolution. Because of this, high throughput primary screens can be directly coupled with high-content secondary screens on the same platform. In effect, the high-content screen becomes a high throughput screen. There is also a dramatic savings in the volumes of costly reagents and drug candidates used in each screening protocol. Furthermore, the delivery of cells to the "wells" is based on specific binding, thus high precision droplets need not be delivered to specific locations. As used herein, the term "wells" does not refer to any depth but merely the location of a cell binding site on the base.

Thus, the present invention provides for unique methods and devices for performing high throughput and high content screening of the physiological response of cells to biologically active compounds, which allows multiple types of cell interactions to be studied simultaneously by combining multicolor luminescence reading, microfluidic delivery, and environmental control of living cells in non-uniform micro-patterned arrays.

SUMMARY OF THE INVENTION

The present invention provides unique devices and methods of performing high throughput and high content screening of the physiological response of cells to biologically active compounds. The present invention allows multiple types of cell interactions to be studied simultaneously by combining multicolor luminescence reading, microfluidic delivery, and environmental control of living cells in non-uniform micro-patterned arrays.

In one embodiment, the present invention encompasses a non-uniform micro-patterned array of cells and methods for making same. The arrays can comprise identical cell types that can be treated with a combinatorial of distinct compounds, or a combinatorial of cell types that can be treated with one or more compounds. By the term combinatorial, it is meant that the wells or groups of wells are variably treated. A further aspect of the present invention comprises a method for analyzing cells, by using the non-uniform micro-patterned cell array of the invention where the cells contain at least one luminescent reporter molecule in combination with a fluid delivery system to deliver a combinatorial of reagents to the micro-patterned array of cells, and means to detect, record and analyze the luminescence signals from the luminescent reporter molecules. In another aspect of the present invention, a cell screening system is disclosed, comprising a luminescence reader instrument for detecting luminescence signals from the luminescent reporter molecules in the non-uniform micro-patterned array of cells, a digital detector for receiving data from the luminescence reader instrument, and a computer means for receiving and processing digital data from the light detector.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

The invention and several of its aspects may be better understood in relation to the following Figures, wherein:

FIG. 1A is a top view of a small substrate micro-patterned chemical array.

FIG. 1B is a top view of a large substrate micro-patterned chemical array.

FIG. 3B is a photograph showing fibroblastic cell growth in spotted patterns, attached to a micro-patterned chemical array and labeled with two fluorescent probes.

FIG. 4 is a diagram of the cassette which is the combination of the non-uniform micro-patterned array of cells top and chamber bottom.

FIG. 18A is a photographic image from High Throughput Mode of luminescence reader instrument identifying "hits".

FIG. 18B is a series of photographic images showing the high content mode identifying high content biological information.

DETAILED DESCRIPTION OF THE PREFERRED EMBODIMENTS

Figure 2:
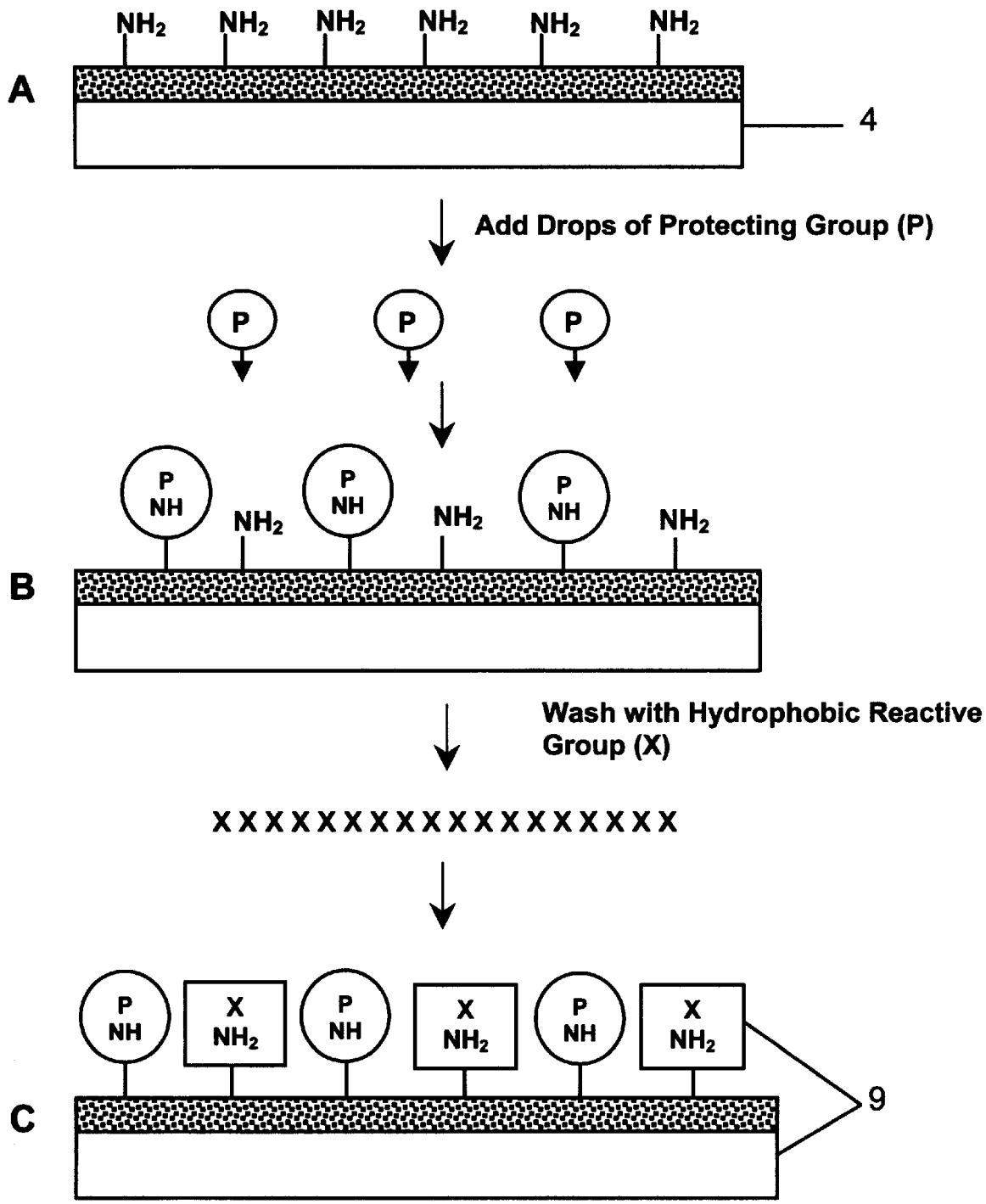
FIG. 2A–C are diagrams of a method of producing a micro-patterned chemical array on a substrate.

In one aspect, the present invention teaches a method of making a non-uniform micro-patterned array of cells on a base. As defined herein, a non-uniform micro-patterned array of cells refers to an array of cells on a base that are not distributed in a single uniform coating on the support surface, but rather in a non-uniform fashion such that each "well" or groups of wells on the support may be unique in its cell binding selectivity.

The method of making a non-uniform micro-patterned array of cells comprises preparing a micro-patterned chemical array, chemically modifying the micro-patterned chemical array non-uniformly, and binding cells to the non-uniform modified micro-chemical array on the base.

In a preferred embodiment, a micro-patterned chemical array comprises a base 4 which is treated to produce a hydrophobic surface across which are dispersed at regular intervals hydrophilic spots or "wells" 8. (FIG. 1A–1B). The base can be a glass, plastic, or silicon wafer, such as a conventional light microscope coverslip, but can also be made of any other suitable material to provide a base. As describe previously, the term "wells" is used to describe a specific spot on the base, and does not require any particular depth. The surface of the base 4 is preferably about 2 cm by 3 cm, but can be larger or smaller. In a preferred embodiment, the wells 8 of the micro-patterned chemical array contain reactable functional groups such as, but not limited to, amino hydroxyl, sulfhydryl or carboxyl groups that can bind to cells non-specifically or be further chemically modified to bind molecules that bind cells specifically.

Modified non-uniform micro-patterned chemical arrays are produced by specific chemical modifications of the wells in the micro-patterned chemical array. The modified array of wells in the non-uniform micro-patterned chemical arrays may contain a variety of different cell binding molecules that permit attachment and growth of cells in the wells. The hydrophobic domains surrounding the wells on the base do not support the attachment and growth of the cells.

In a preferred embodiment a non-uniform micro-patterned array of cells is made by coating a glass wafer via chemisorbance with a layer of a substance having reactable functional groups such as amino groups. In a preferred embodiment, an aminosilane such as 3-amino propyltrimethoxysilane (APTS) or N-(2-aminoethyl-3-aminopropyl) timethoxysilane (EDA) is used, but other reactable substances may be used. Following this first step, due to the presence of the reactable functional groups, the entire surface of the coated glass wafer is hydrophilic.

Secondly, a micro-patterning reaction is carried out where drops containing a substance having photocleavable or chemically removable amino protecting groups are placed in a micro-pattern of discrete locations on the aminosilane coated glass wafer. In one embodiment the pattern comprises a rectangular or square array, but any suitable discrete pattern, may be used (such as, but not limited to, triangular or circular). In one embodiment, the drops range in volume from 1 nanoliter (nl) to 1000 nl. In a preferred embodiment the drops range from 250–500 nl in volume. Suitable photochemically removable amino protecting substances include, but are not limited to 4-bromomethyl-3-nitrobenzene, 1-(4,5-dimethoxy-2-nitrophenyl)-ethyl (DMNPE) and butyloxycarbonyl. In one embodiment, the patterning reaction is carried out for 1 to 100 minutes at temperatures ranging from ambient temperature to 37° C., using reagent concentrations of between 1 micromolar (uM) and 1000 uM. In a preferred embodiment, the reaction is carried out at 37° C. for 60 minutes using a reagent concentration of 500 uM.

The drops may be placed onto the aminosilane coated glass wafer via conventional ink-jet technology. (U.S Pat. No. 5,233,369; U.S. Pat. No. 5,486,855, both references herein incorporated by reference). Alternatively, an array of pins, defined herein as tapered rods that can transfer between 1 nl and 1000 nl of fluid, is dipped into a bath of the amino protecting substance to produce drops of the protecting substance on their ends. The pins are then contacted with the glass wafer to transfer the drops thereto. In another embodiment, an array of capillary tubes made of glass or plastic, as described in U.S Pat. Nos. 5,567,294 and 5,527,673, (both herein incorporated by reference), containing the amino protecting substance is contacted with the glass wafer to transfer the droplets to the surface. Thus, the glass wafer is micro-patterned with an array of spots or wells that contain protected amino groups on a hydrophobic surface (FIG. 2A–B).

Third, a hydrophobic substance reactive with unprotected amino groups is washed over the glass wafer. The hydrophobic substance can be a fatty acid or an alkyl iodide, or any other suitable structure. Certain conditions for such a derivatization of glass can be found in Prime and Whitesides, Science 252:1164–1167, 1991, Lopez et al., J. Am. Chem. Soc. 115:5877–5878, 1993, and Mrksich and Whitesides, Ann. Rev. Biophys. Biomol. Struct. 25:55–78, 1996. The fatty acid or alkyl iodide reacts with the unprotected amino groups and covalently attaches thereto, and the amino groups are now hydrophobic due to the fatty acid or alkyl iodide group. The resulting micro-patterned chemical array 9 comprises a glass wafer 4 with an array of wells 8 containing protected amino groups on a hydrophobic background. (FIG. 2C).

Fourth, the modified non-uniform micro-patterned chemical array is produced by uniformly deprotecting the amino groups in a micro-patterned chemical array produced according to the above-described methods. In one embodiment, chemical specificity can be added by chemically crosslinking specific molecules to the wells. There are a number of well known homo- or hetero-bifunctional crosslinking reagents such as ethylene glycol bis (succinimidylsuccinate) that will react with the free amino groups in the wells and crosslink to a specific molecule. Reagents and conditions for crosslinking free amino groups with other biomolecules are well known in the art, as exemplified by the following references: Grabarek and Gergely, Analyt. Biochem 185:131–135, 1990; McKenzie et al., J. Prot. Chem. 7:581–592, 1988; Brinkley, Bioconjugate Chem. 3:12–13; 1992, Fritsch et al., Bioconjugate Chem. 7:180–186, 1996; and Aplin and Hughes, 1981.

In a preferred embodiment, a modified micro-patterned chemical array is produced in combinatorial fashion. The resulting wells are non-uniform (i.e., each well or group of wells may be unique in its cell binding selectivity). By the term combinatorial, it is meant that the wells are variably treated.

In one embodiment, the protected amino groups of the micro-patterned chemical array of step 3 are deprotected and then specific molecules with chemical crosslinking reagents are deposited in a desired pattern. The specific crosslinking agents can bind to the amino groups and further possess a cell-binding group. In this step, the type of cell binding group can be varied, from well to well or from group of wells to group of wells, to create a non-uniform design in the array.

In another embodiment, the amino groups of the micro-patterned chemical array of step 3 are uniformly deprotected. A photo-activatable crosslinker is reacted with the deprotected amino groups. An optical mask of a desired pattern is placed over the surface of the wells and the exposed wells are illuminated with a light source. The position and number of wells which receive light is controlled by the micro-pattern of the optical mask. Suitable photoactivatable crosslinkers include aryl nitrenes, fluorinated aryl azides, benzophenones, and diazopyruvates. Reagents and conditions for optical masking and crosslinking are discussed in Prime and Whitesides, 1991; Sighvi et al., 1994, Sigal et al., 1996 and Mrksich and Whitesides, 1996. The photoactivatable crosslinker is bi-functional in that it chemically bonds to the amino group on the wells and, when exposed to light, covalently bonds to cell binding molecules, such as antibodies. Reagents and conditions for photoactivated crosslinking are discussed in Thevenin et al., Eur. J. Biochem. 206:471–477, 1992 and Goldmacher et al., Bioconjugate Chem. 3:104–107, 1992.

When a photo-activatable crosslinker is used, the glass plate is flooded with cell binding molecules to be bound to the wells. In one embodiment, cell binding molecules such as cell surface antigen-reactive antibodies, extracellular matrix proteins, (for example, fibronectin or collagen) or charged polymers (for example poly-L-lysine or poly-L-arginine) are used in concentrations ranging from about 0.1 to about 1 mM. While the cell binding molecules cover the wells, the glass plate is irradiated from the underside of the glass plate, at an angle below the critical angle of the material of the glass plate, resulting in total internal reflection of the light (For discussion of total internal reflection fluorescence microscopy, see Thompson et al., 1993). In one embodiment, the irradiation is carried out at between ambient temperature and 37° C. for 0.1 to 10 seconds with light of wavelength between 300 nanometers (rm) to 1000 nm. In a preferred embodiment, the irradiation is conducted at ambient temperature for 1 second using light with a wavelength of between about 300 and 400 mn. Optical crosslinking limits the photo-activatable crosslinking to a short distance into the solution above the wells, and is described in Bailey et al., Nature 366:44–48, 1993; Farkas et al., Ann. Rev. Physiol. 55:785–817, 1993; Taylor et al., Soc. Opt. Instr. Eng. 2678:15–27, 1996; Thompson et al., in Mason, W. T. (ed.), "Fluorescent and Luminescent Probes for Biological Activity." San Diego: Academic Press pp. 405–419, 1993.

The photo-activatable crosslinker binds with the cell binding molecules such as antibodies and matrix proteins, only in the wells where the crosslinker was irradiated. For example, a single row of an array of wells can be irradiated to produce a single row of wells with cell binding molecules bound to the crosslinker. Following a washing of the array to eliminate any unbound cell binding molecule, a second row of wells can be bound to a second cell binding molecule by subsequent flooding of the glass wafer with the second cell binding molecule while irradiating the second row and optically masking the other rows. Unbound cell binding molecules are removed by washing the array with PBS, or any other suitable buffer. In this fashion, multiple rows of wells or groups of wells can be sequentially illuminated by sequential masking in the presence of a particular cell binding molecule. Alternatively, each well can be irradiated one by one using pinpoint exposure and optical asking. In this manner, different cell binding molecules are bound to rows of the array or to individual wells, creating a non-uniform micro-array of cells of any desired pattern.

In a further embodiment for producing modified micro-patterned chemical arrays, a micro-patterned chemical array is first produced wherein the amino groups of the wells are uniformly protected with photocleavable protecting groups. Rows, columns, and/or individual wells are sequentially photo-deprotected to expose the free amino groups by using an optical mask of various patterns to cover all but the wells to be deprotected. The exposed wells (i.e., those not covered by the mask), are illuminated, resulting in removal of the protecting groups. The array is flooded with a bifunctional crosslinker which chemically bonds to the deprotected amino group and activates the wells. Conditions for the photodeprotection of amino groups are discussed in Pillai, In Padwa, A. (ed.) "Organic Photochemistry.", New York 9:225–323, 1987, Ten et al., Makromol. Chem. 190:69–82, 1989, Pillai, Synthesis 1980:1–26, 1980, Self and Thompson, Nature Medicine 2:817–820, 1996 and Senter et al., Photochem. Photobiol. 42:231–237, 1985. Next, cell binding molecules are flooded onto the modified chemical array wherein they react with the other half of the crosslinker. The array is then washed to eliminate any unbound bifunctional crosslinker and cell binding molecules. Another well or set of wells may be deprotected using another optical mask, and the array may then be flooded with a second treatment of a bifunctional crosslinker followed by a distinct cell binding molecule which bonds to this second well or set of wells of deprotected amino groups. The array is washed to eliminate the second treatment of a bifunctional crosslinker and cell binding molecules. A non-uniform array of cell binding molecules may thus be produced by a repeated sequence of photo-deprotection, chemical crosslinking of specific molecules and washing under a variety of masks. Alternatively, the crosslinking reagents can be delivered to the deprotected wells together with the cell binding molecules in one step. Concentration gradients of attached cell binding molecules can be created by controlling the number of deprotected amino groups exposed using an optical mask, or by controlling the dose of irradiation for the photoactivatable crosslinkers.

The modified micro-patterned chemical array is then used to produce a non-uniform micro-patterned array of cells. In one embodiment, the modified micro-patterned chemical array is "seeded" with cells by introducing suspended cells onto the array, allowing binding of the cells to the wells and then rinsing the wafer to remove unbound and weakly bound cells. The cells are bound only in the wells, because the specific chemical environment in the wells, in conjunction with the hydrophobic environment surrounding each of the wells, permits the selective binding of cells to the wells only.

Furthermore, the modification of wells with specific cell-binding molecules permits selective binding of cells to specific wells, producing a non-uniform micro-patterned array of cells. In addition, the cell surface molecules that specifically bind to the wells may be either naturally present or genetically engineered by expressing "well-binding" molecules that have been fused to cellular transmembrane molecules such that cells interact with and bind specifically to modified wells. The creation of an array of wells with different cell recognition molecules allows one well, a group of wells or the entire array to specifically "recognize", grow and screen cells from a mixed population of cells.

In one embodiment, cells suspended in culture medium at concentrations ranging from about $10^3$ to about $10^7$ cells per ml are incubated in contact with the wells for 1 to 120 minutes at temperatures ranging from ambient temperature to 37° C. Unbound cells are then rinsed off of the wells using culture medium or a high density solution to lift the unbound cells away from the bound cells. (Channavajjala, et al., J. Cell Sci. 110:249–256, 1997). In a preferred embodiment, cells suspended in culture medium at concentrations ranging from about $10^5$ to about $10^6$ cells per ml are incubated in contact with the wells at 37° C. for times ranging from about 10 minutes to about 2 hours.

The density of cells attached to the wells is controlled by the cell density in the cell suspension, the time permitted for cell attachment to the chemically modified wells and/or the density of cell binding molecules in the wells. In one embodiment of the cell attachment procedure, $10^3$- to $10^7$ cells per ml are incubated at between ambient temperature and 37° C. for between 1 minute and 120 minutes, with wells containing between 0.1 and 100 mmoles per $cm^2$ of cell binding molecules. In a preferred embodiment, $10^5$ and $10^6$ cells per ml are incubated for 10 minutes to 2 hours at about 37° C., with wells containing about 10 to 100 nmoles per $cm^2$ of cell binding molecules.

In one embodiment, the cells may be chemically fixed to the wells as described by Bell et al., J. Histochem. Cytochem 35:1375–1380, 1987; Poot et al., J. Histochem. Cytochem 44:1363–1372, 1996; Johnson, J. Elect. Micros. Tech. 2:129–138, 1985, and then used for screening at a later time with luminescently labeled molecules such as antibodies, nucleic acid hybridization probes or other ligands.

In another embodiment, the cells can be modified with luminescent indicators of cell chemical or molecular properties, seeded onto the non-uniform micro-patterned chemical array and analyzed in the living state. Examples of such indicators are provided in Giuilano et al., Ann. Rev. Biophys. Biomol. Struct. 24:405–434, 1995; Harootunian et al., Mol. Biol. Cell 4:993–1002, 1993; Post et al., Mol. Biol. Cell 6:1755–1768, 1995; Gonzalez and Tsien, Biophys. J. 69:1272–1280, 1995; Swaminathan et al., Biophys. J. 72:1900–1907, 1997 and Chalfie et al., Science 263:802–805, 1994. The indicators can be introduced into the cells before or after they are seeded onto the array by any one or a combination of variety of physical methods, such as, but not limited to diffusion across the cell membrane (reviewed in Haugland, Handbook of fluorescent probes and research chemicals, $6^{th}$ ed. Molecular Probes, Inc., Eugene, 1996), mechanical perturbation of the cell membrane (McNeil et al., J. Cell Biology 98:1556–1564, 1984; Clarke and McNeil, J. Cell Science 102:533–541, 1992; Clarke et al., BioTechniques 17:1118–1125, 1994), or genetic engineering so that they are expressed in cells under prescribed conditions. (Chalfie et al., 1994). In a preferred embodiment, the cells contain luminescent reporter genes, although other types of reporter genes, including those encoding chemiluminescent proteins, are also suitable. Live cell studies permit analysis of the physiological state of the cell as reported by luminescence during its life cycle or when contacted with a drug or other reactive substance.

Figure 3A:
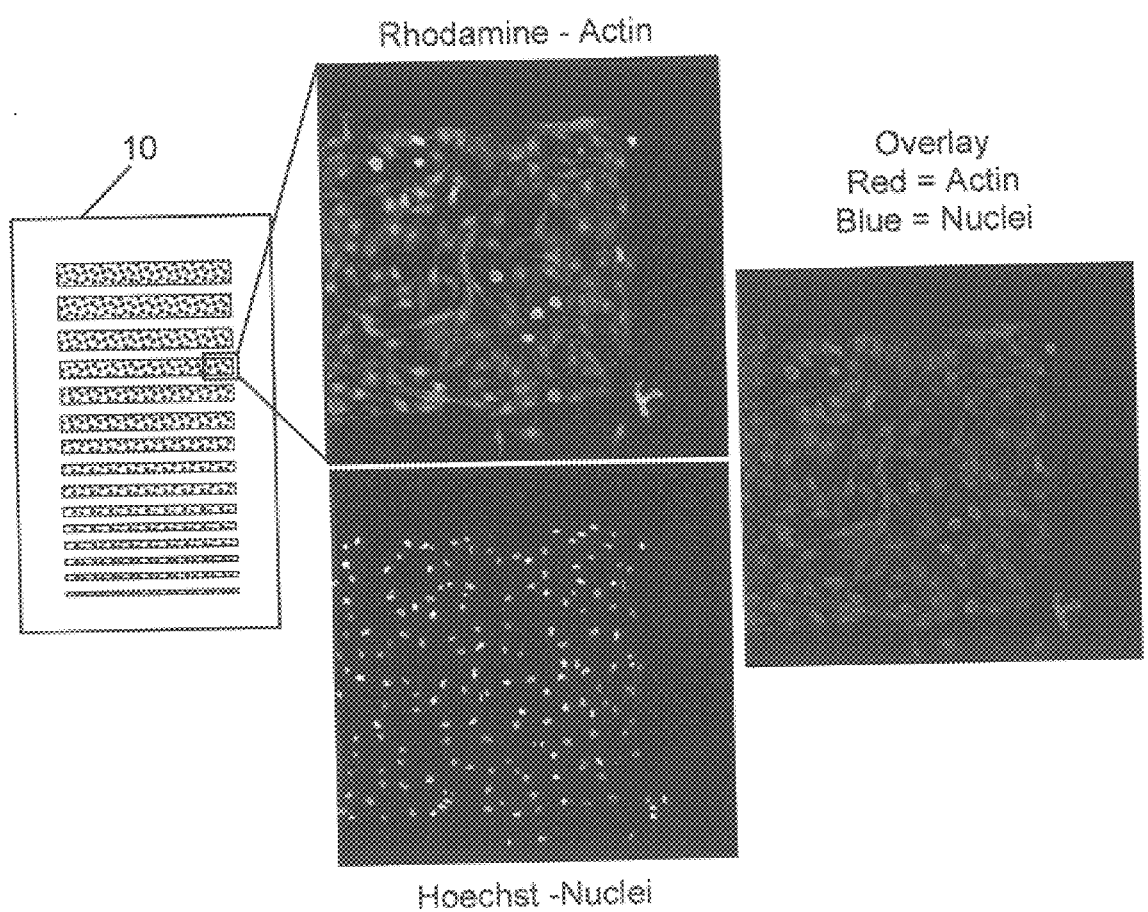
FIG. 3A is a photograph showing fibroblastic cell growth on a surface patterned chip, attached to a micro-patterned chemical array and labeled with two fluorescent probes.

In another aspect of the present invention, a non-uniform micro-patterned cell array is provided, wherein cells are non-uniformly bound to a modified micro-patterned chemical array in wells on a base. The non-uniform micro-patterned array of cells is non-uniform because the underlying non-uniform modified chemical array provides a variety of cell binding sites of different specificity. Any cell type can be arrayed on the non-uniform micro-patterned array of cells, providing that a molecule capable of specifically binding that cell type is present in the micro-patterned chemical array. Preferred cell types for the non-uniform micro-patterned array of cells include lymphocytes, cancer cells, neurons, fungi, bacteria and other prokaryotic and eukaryotic organisms. For example, FIG. 3A shows a non-uniform micro-patterned array of cells containing fibroblastic cells grown on a surface patterned chip and labeled with two fluorescent probes (rhodamine to stain actin and Hoechst to stain nuclei), while FIG. 3B shows a non-uniform micro-patterned array of cells containing fibroblastic cell growth (L929 and 3T3 cells) in spotted patterns, labeled with two fluorescent probes and visualized at different magnifications. Examples of cell-binding molecules that can be used in the non-uniform micro-patterned array of cells include, but are not limited to antibodies, lectins and extracellular matrix proteins. Alternatively, genetically engineered cells that express specific cell surface markers can selectively bind directly to the modified wells. The non-uniform micro-patterned array of cells may comprise either fixed or living cells. In a preferred embodiment, the non-uniform micro-patterned array of cells comprises living cells such as, but not limited to, cells "labeled" with luminescent indicators of cell chemical or molecular properties.

In another aspect of the present invention, a method for analyzing cells is provided, comprising preparing a non-uniform micro-patterned array of cells wherein the cells contain at least one luminescent reporter molecule, contacting the non-uniform micro-patterned array of cells to a fluid delivery system to enable reagent delivery to the non-uniform micro-patterned array of cells, conducting high-throughput screening by acquiring luminescence image of the entire non-uniform micro-patterned array of cells at low magnification to detect luminescence signals from all wells at once to identify wells that exhibit a response. This is followed by high-content detection within the responding wells using a set of luminescent reagents with different physiological and spectral properties, scanning the non-uniform micro-patterned array of cells to obtain luminescence signals from the luminescent reporter molecules in the cells, converting the luminescence signals into digital data and utilizing the digital data to determine the distribution, environment or activity of the luminescent reporter molecules within the cells.

Preferred embodiments of the non-uniform micro-patterned array of cells are disclosed above. In a preferred embodiment of the fluid delivery system, a chamber, mates with the base containing the non-uniform micro-patterned array of cells. The chamber is preferably made of glass, plastic or silicon, but any other material that can provide a base is suitable. One embodiment of the chamber 12 shown in FIG. 4 has an array of etched domains 13 matching the wells 4 in the non-uniform micro-patterned array of cells 10. In addition, microfluidic channels 14 are etched to supply fluid to the etched domains 13. A series of "waste" channels 16, to remove excess fluid from the etched domains 13, can also be connected to the wells. The chamber 12 and non-uniform micro-patterned array of cells 10 together constitute a cassette 18.

The chamber 12 is thus used for delivery of fluid to the non-uniform micro-patterned array of cells 10. The fluid can include, but is not limited to a solution of a particular drug, protein, ligand, or other substance which binds with surface expressed moieties of cells or that are taken up by the cells. The fluid to interact with the non-uniform micro-patterned array of cells 10 can also include liposomes encapsulating a drug. In one embodiment, such a liposome is formed from a photochromic material, which releases the drug upon exposure to light, such as photoresponsive synthetic polymers. (Reviewed in Willner and Rubin, Chem. Int. Ed. Engl. 35:367–385, 1996). The drug can be released from the liposomes in all channels 14 simultaneously, or individual channels or separate rows of channels may be illuminated to release the drug sequentially. Such controlled release of the drug may be used in kinetic studies and live cell studies. Control of fluid delivery can be accomplished by a combination of micro-valves and micro-pumps that are well known in the capillary action art. (U.S. Pat. No. 5,567,294; U.S. Pat. No. 5,527,673; U.S. Pat. No. 5,585,069, all herein incorporated by reference.)

Figure 5:
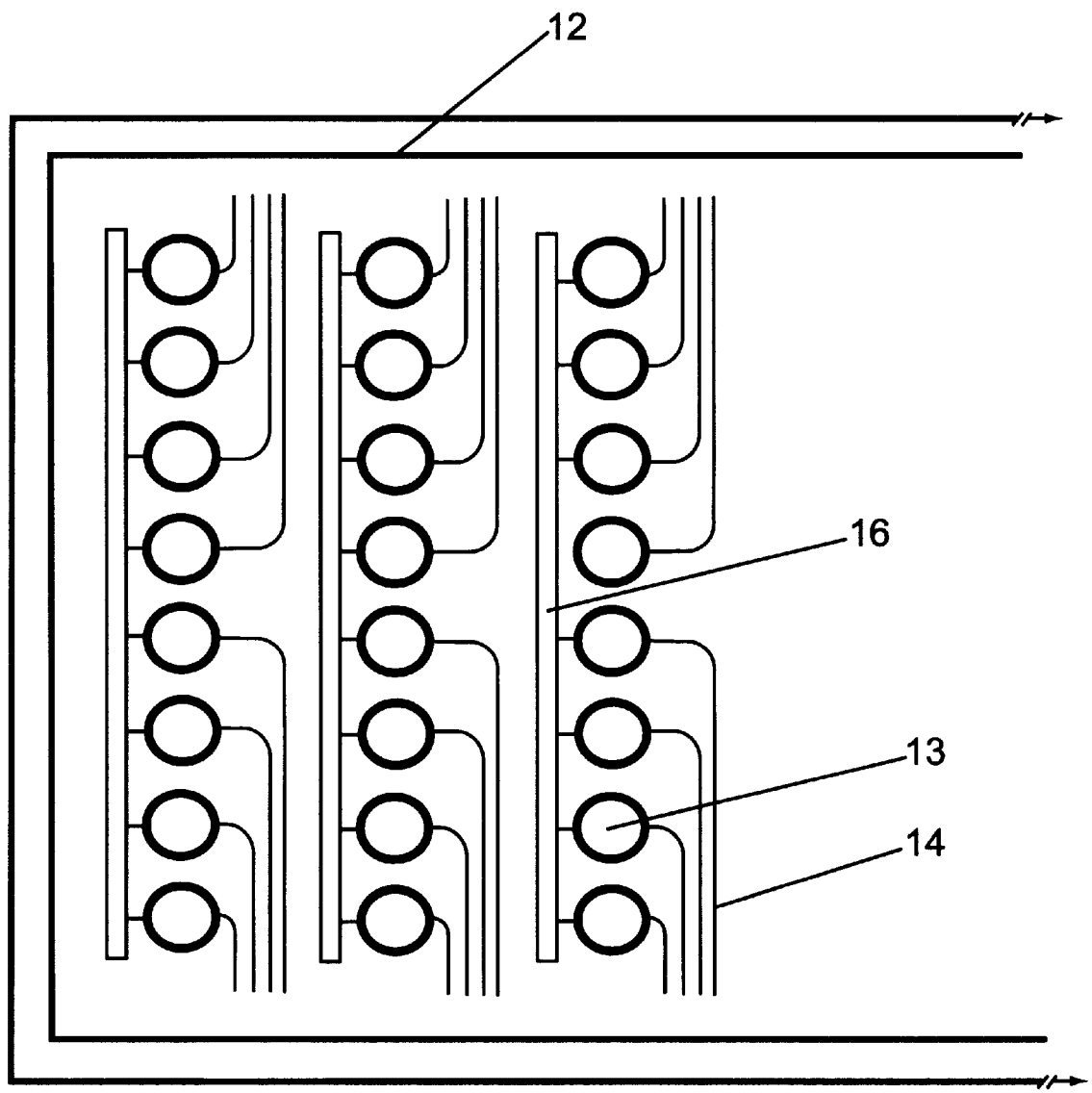
FIG. 5 is a diagram of a chamber that has nanofabricated microfluidic channels to address "wells" in the non-uniform micro-patterned array of cells.
Figure 6:
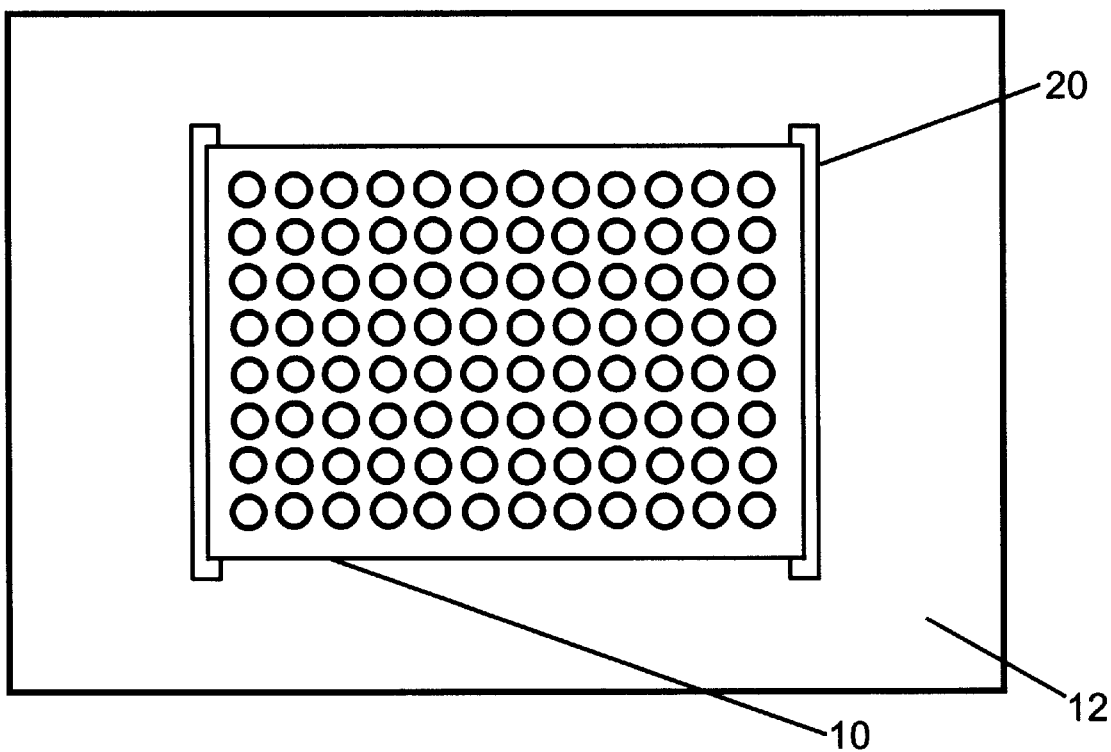
FIG. 6 is a diagram of a chamber with no channels.

Another embodiment of the chamber 12 shown in FIG. 5 has an array of microfluidic channels 14 matching the chamber's etched domains 13 which are slightly larger in diameter than the wells 8 of the non-uniform micro-patterned array of cells 10, so that the wells 4 are immersed into the etched domains 13 of the chamber 12. Spacer supports 20 are placed between the chamber 12 and the non-uniform micro-patterned array of cells 10 along the sides of contact. The non-uniform micro-patterned array of cells 10 and the chamber 12 can be sealed together using an elastomer or other sticky coating on the raised region of the chamber. Each etched domain 13 of the chamber 12 can be individually or uniformly filled with a medium that supports the growth and/or health of the cells in the non-uniform micro-patterned array of cells 10. In a further embodiment (FIG. 6), the chamber contains no microfluidic channels, for treating all the wells of the non-uniform micro-patterned array of cells 10 with the same solution.

Figure 7:
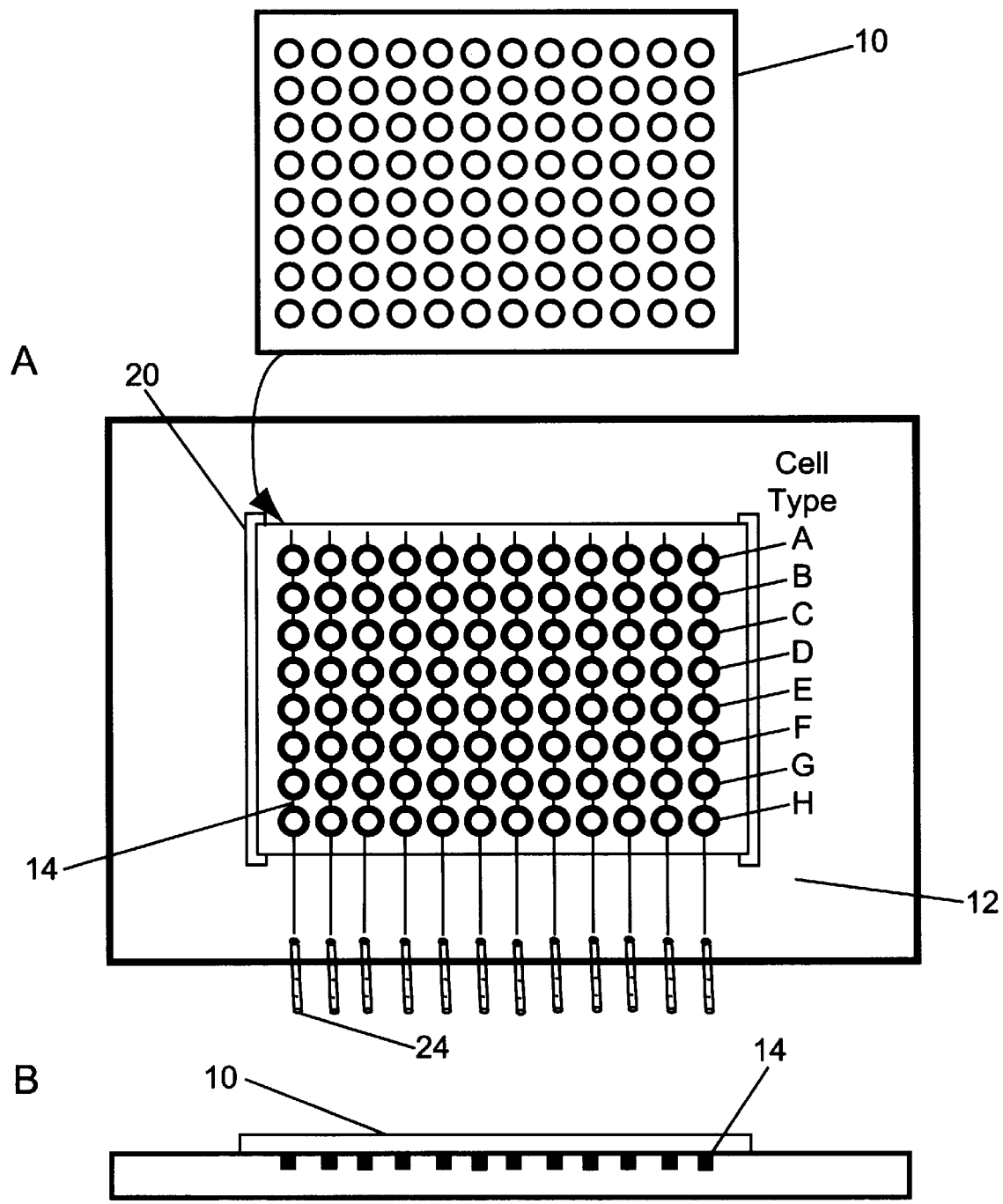
FIG. 7A is an overhead diagram of a chamber with microfluidic channels etched onto the substrate.
FIG. 7B is a side view diagram of a chamber with microfluidic channels etched onto the substrate.

Delivery of drugs or other substances is accomplished by use of various modifications of the chamber as follows. A solution of the drug to be tested for interaction with cells of the array can be loaded from a 96 well microtiter plate into an array of microcapillary tubes 24. (FIG. 7). The array of microcapillary tubes 24 corresponds one-to-one with the microfluidic channels 14 of the chamber 12, allowing solution to flow or be pumped out of the microcapillary tubes 24 into the channels 14. The non-uniform micro-patterned array of cells 10 is inverted so that the wells 8 become submerged in the etched domain 13 filled with the fluid (FIG. 7B). Once the interaction between the fluid and non-uniform micro-patterned array of cells 10 occurs, luminescence signals emanating from the non-uniform micro-patterned array of cells 10 can be measured directly or, alternatively, the non-uniform micro-patterned array of cells 10 can be lifted off the chamber for post processing, fixation, and labeling. The placement and removal of the array of cells may be accomplished via robotics and/or hydraulic mechanisms. (Schroeder and Neagle, 1996).

In one embodiment of the chamber 12 shown in FIG. 7, the channels and matching etched domains 13 are etched into the chamber chemically (Prime and Whitesides, 1991; Lopez et al., 1993; Mrksich and Whitesides, 1996). The etched domains 13 are larger in diameter than the wells 8 of the non-uniform micro-patterned array of cells 10. This permits the chamber 12 to be contact sealed to the non-uniform micro-patterned array of cells 10, leaving space for the cells and a small volume of fluid. Microfluidic channels 14 are etched into each row of etched domains 13 of the chamber 12. Each microfluidic channel 14 extends from two opposing edges of the chamber 12 and is open at each edge. The etched domains 13 of a single row are in fluid communication with the channels 14 by placing a microcapillary tube 24 containing a solution into contact with the edge of the chamber 12. Each row of connected channels 14 can be filled simultaneously or sequentially. During filling of the channels 14 by valves and pumps or capillary action, each of the channels of the chamber 12 fills and the drug passes to fill each etched domain 13 in the row of etched domains 13 connected by the channel 14.

Figure 8:
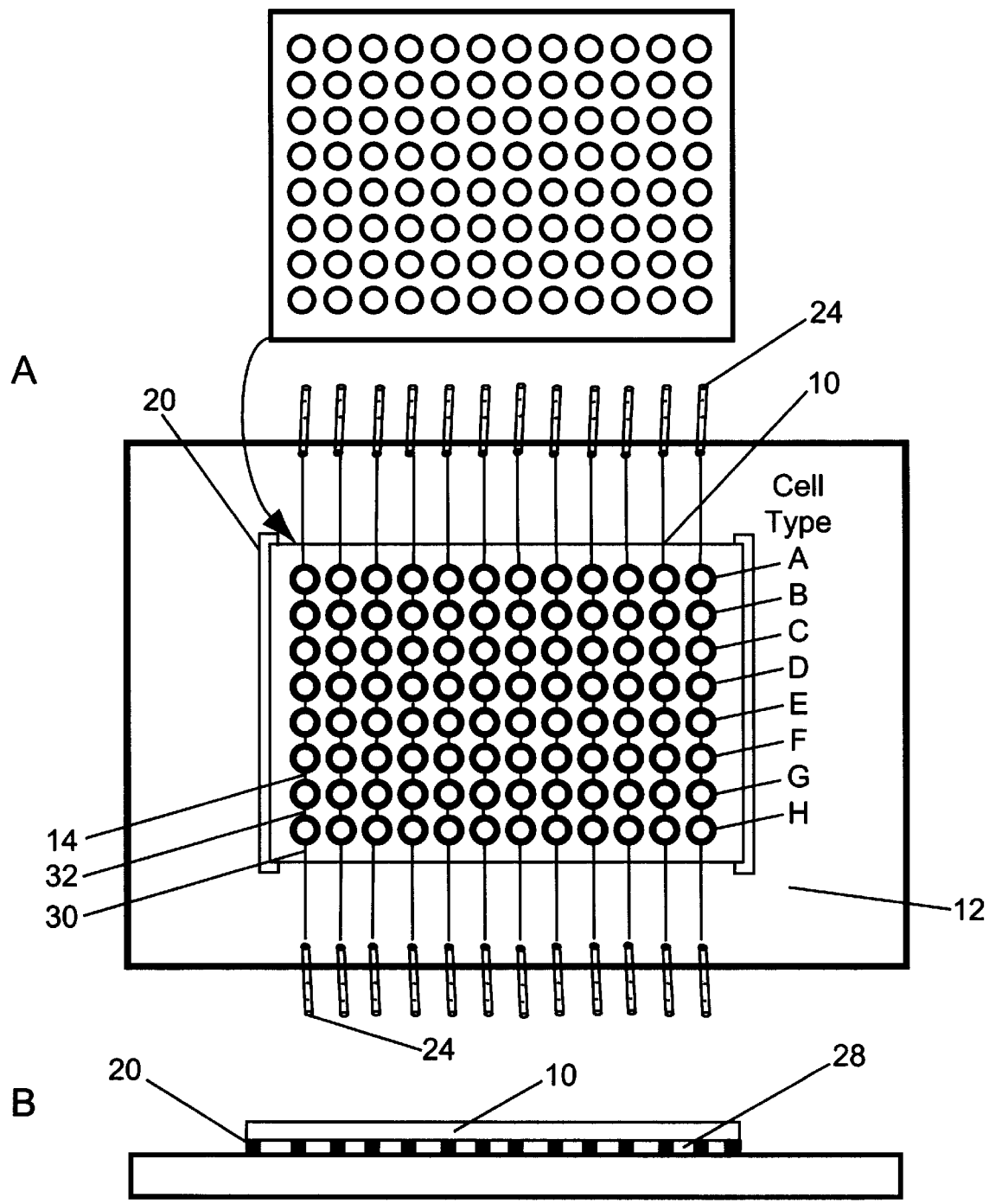
FIG. 8A is an overhead diagram of a chamber where the microfluidic channels and wells are formed from a raised matrix of a material stamped onto the fluid delivery chamber.
FIG. 8B is a side view diagram of a chamber where the microfluidic channels and wells are formed from a raised matrix of a material stamped onto the fluid delivery chamber.

In a further embodiment of the chamber 12, raised reservoirs 28 and channels 14 can be placed onto the surface of the chamber 12 as shown in FIG. 8b. In a preferred embodiment, the raised reservoirs 28 and channels 14 can be made from polytetrafluoroethylene or elastomeric material, but they can be made from any other sticky material that permits attachment to the non-uniform micro-patterned array of cells 10, such as poly(dimethylsiloxane), manufacture by Dow Corning under the trade name Sylgard 184™. The effect is the same as with a chamber having etched channels and channels and its uses are similar.

In another embodiment of the chamber shown in FIG. 8A, a first channel 30 extends from one edge of the chamber 12 to a first etched domain 13 or raised reservoirs 28 and channels. A second channel 32 extends from the opposing edge to a second etched domain adjacent the first etched domain. The first 30 and second 32 channels are not in fluid communication with each other yet are in the same row of channels 14 or raised reservoirs 28.

Figure 9:
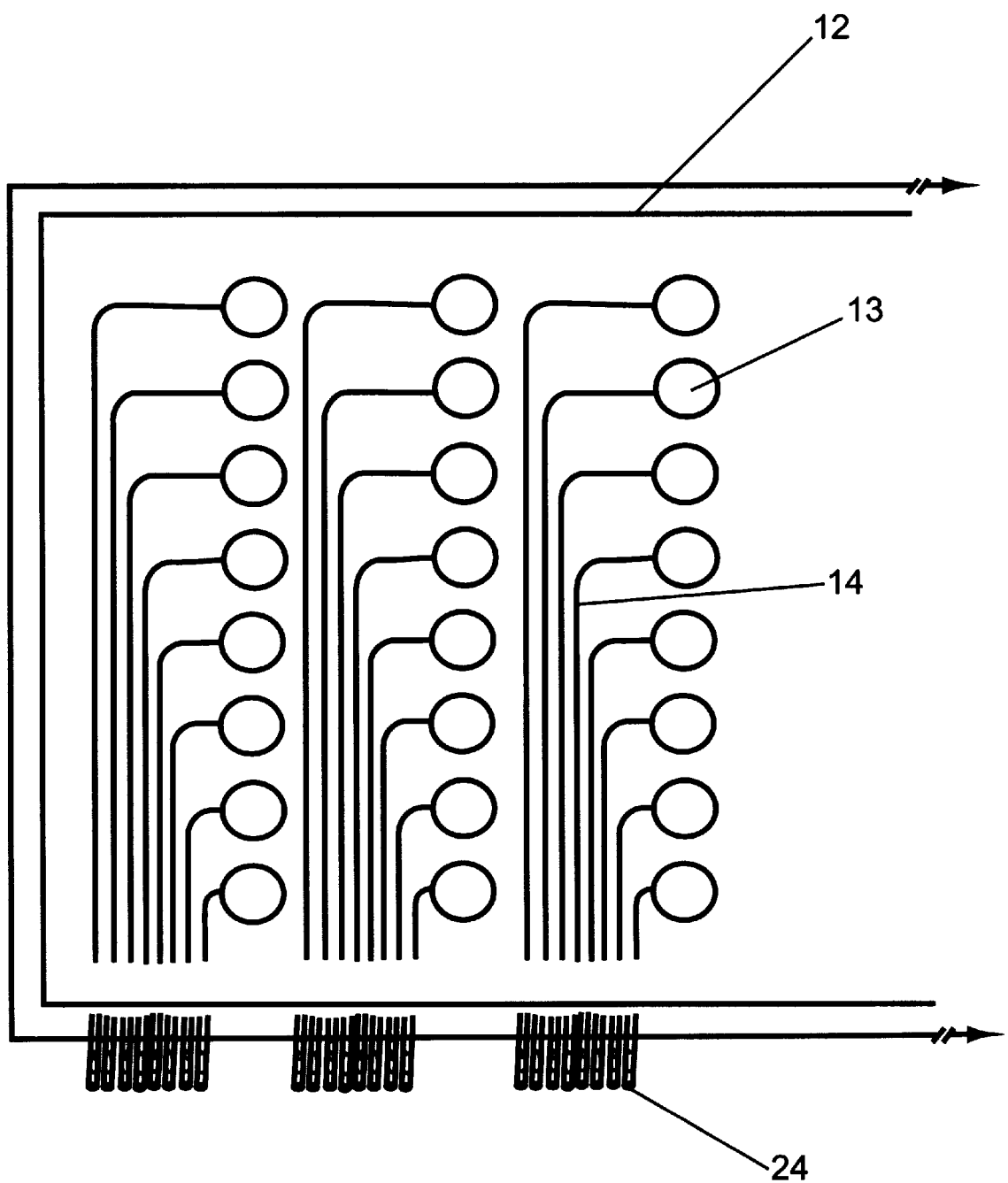
FIG. 9 is a diagram of a chamber where each well is addressed by a channel originating from one side of the chamber.
Figure 10:
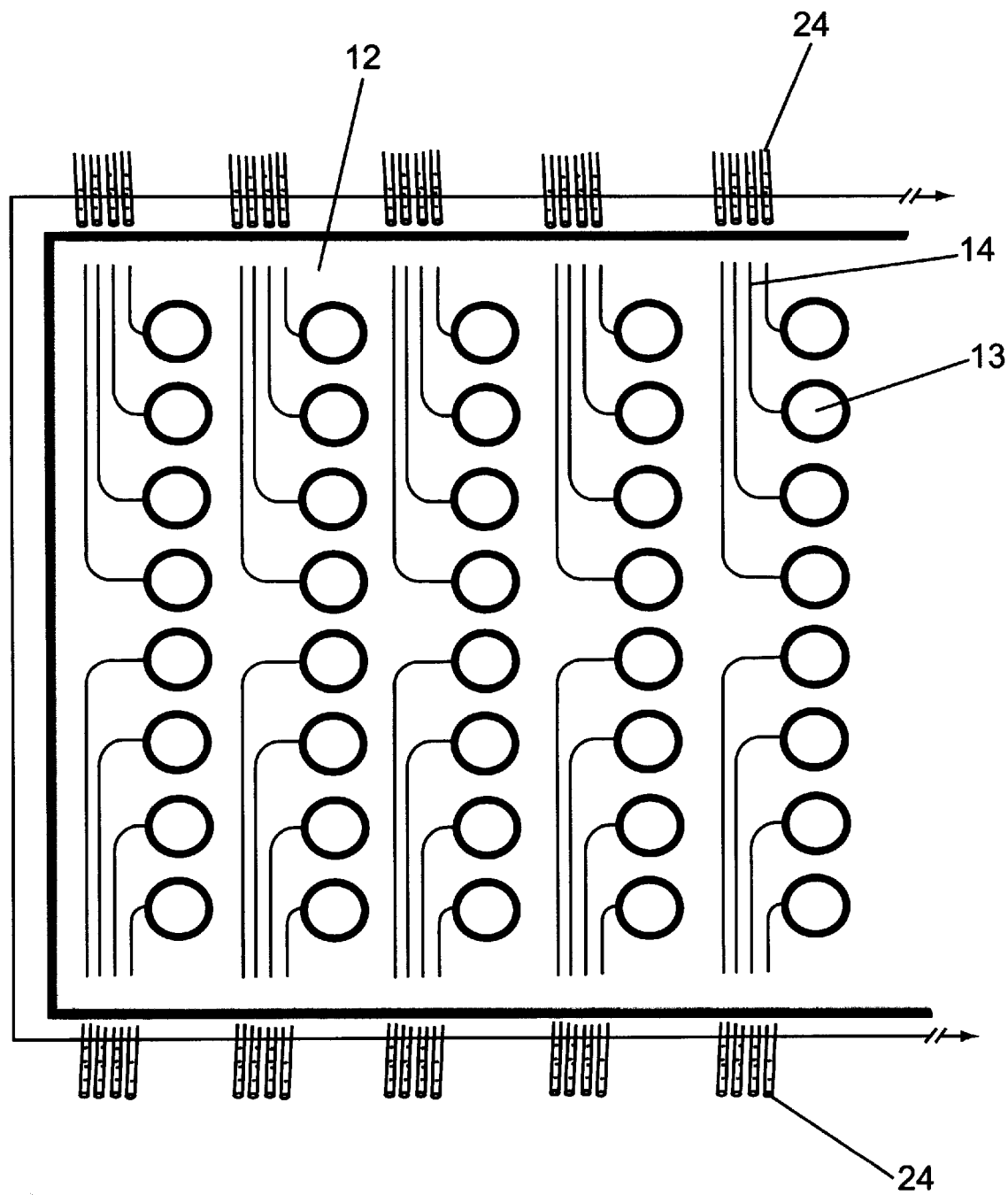
FIG. 10 is a diagram of a chamber where the wells are addressed by channels originating from two sides of the chamber.

In another embodiment, as shown in FIGS. 9 and 10, the chamber 12 may have a channel 14 extending from each etched domain 13 or raised reservoir 28 to the edge of the chamber. The channels 14 can all originate from one edge of the chamber 12 (FIG. 9), or from both edges (FIG. 10). The channels 14 can also be split to both sides of the etched domains 13 to minimize the space occupied by the channels 14. Separate fluidic channels allow for performance of kinetic studies where one row at a time or one depression at a time is charged with the drug.

Figure 11:
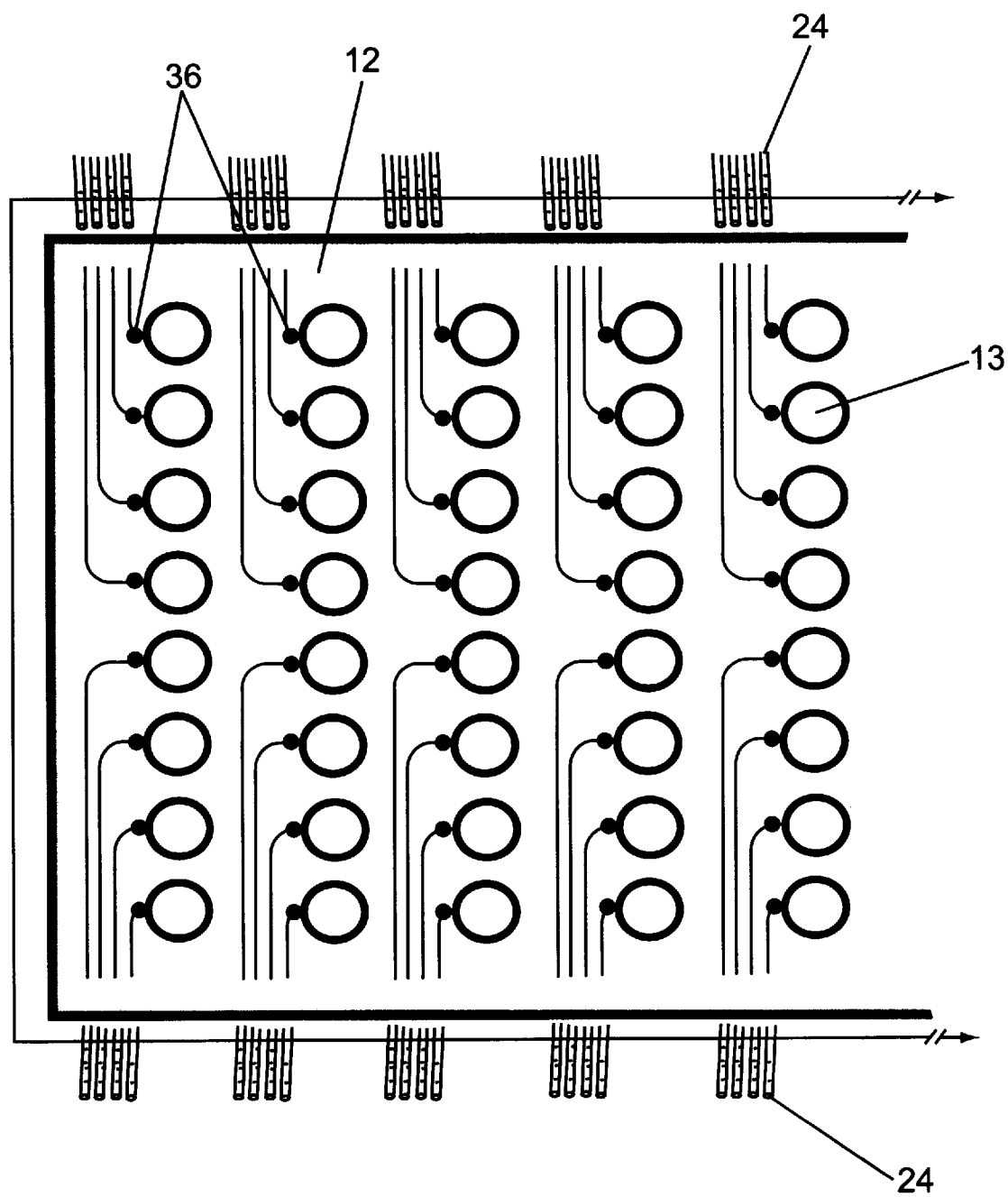
FIG. 11 is a diagram of a chamber where the microfluidic switches are controlled by light, heat or other mechanical means.

In a further embodiment depicted in FIG. 11, each etched domain 13 is in fluid communication with a corresponding channel 14 having a plug 36 between the end of the channel 14 and the etched domain 13, which prevents the injected solution from flowing into the etched domain 13 until the desired time. Solutions may be preloaded into the channels 14 for use at a later time. A plug 36 likewise can be disposed between a terminal etched domain 13 in a set of connected etched domains 13 in fluid communication with a channel 14. Upon release of the plug 36, the substance flows through and fills all the etched domains 13 which are in fluid communication with the channel 14.

In one embodiment, the plugs 36 are formed of a hydrophobic polymer, such as, but not limited to proteins, carbohydrates or lipids that have been crosslinked with photocleavable crosslinkers that, upon irradiation, becomes hydrophilic and passes along with the drug into the depression. Alternatively, the plug 36 may be formed of a crosslinked polymer, such as proteins, carbohydrates or lipids that have been crosslinked with photocleavable crosslinkers that, when irradiated, decomposes and passes into the etched domain 13 along with the solution.

Figure 12:
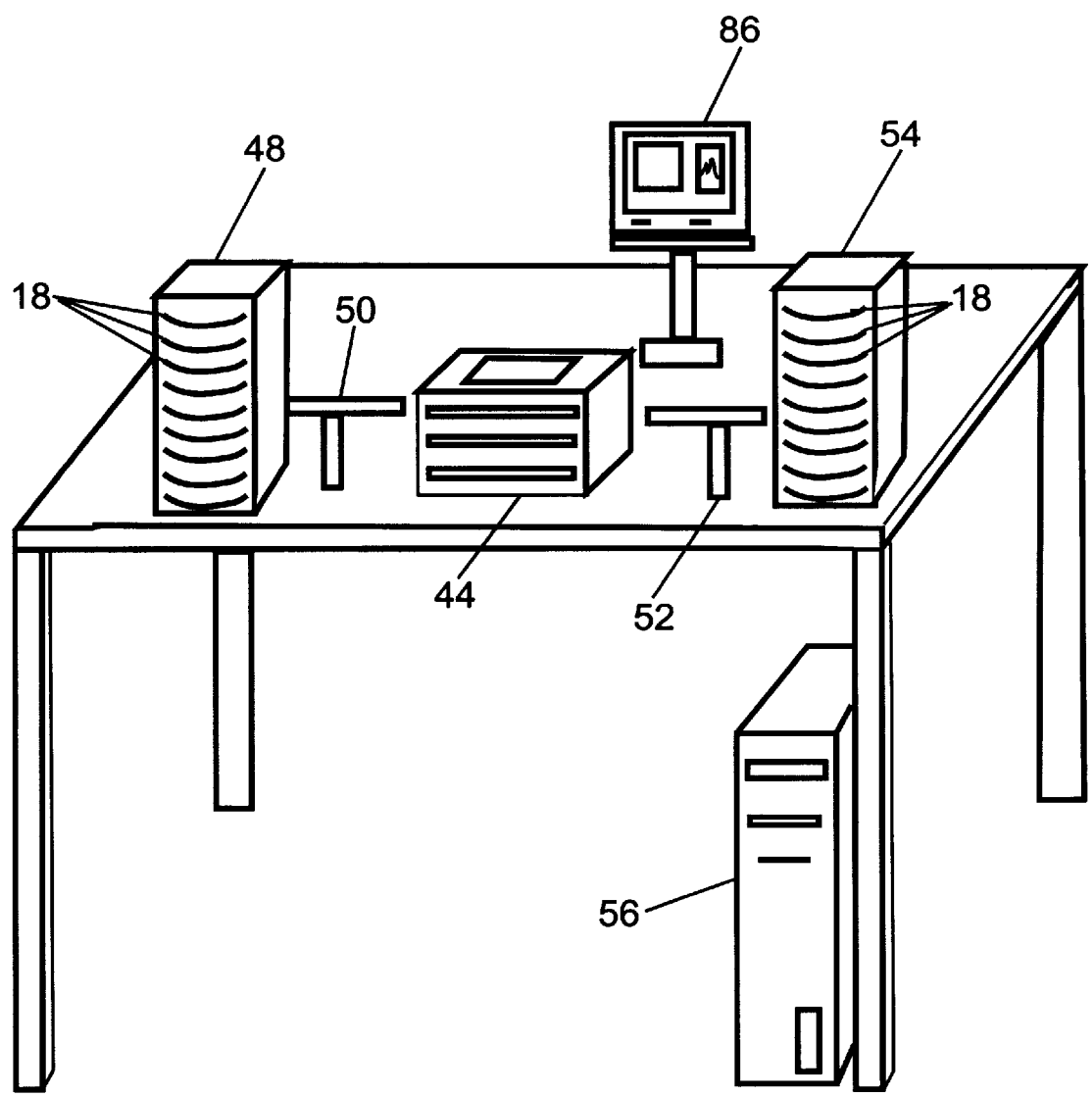
FIG. 12 is a diagram of the luminescence reader instrument, which is a modified integrated circuit inspection station using a fluorescence microscope as the reader and small robots to manipulate cassettes.

The cassette 18, which comprises of the non-uniform micro-patterned array of cells 10 and the chamber 12 is inserted into a luminescence reader instrument. The luminescence reader instrument is an optical-mechanical device that handles the cassette, controls the environment (e.g., the temperature, which is important for live cells), controls delivery of solutions to wells, and analyzes the luminescence emitted from the array of cells, either one well at a time or the whole array simultaneously. In a preferred embodiment (FIG. 12), the luminescence reader instrument comprises an integrated circuit inspection station using a fluorescence microscope 44 as the reader and microrobotics to manipulate the cassettes. A storage compartment 48 holds the cassettes 18, from where they are retrieved by a robotic arm 50 that is controlled by computer 56. The robotic arm 50 inserts the cassette 18 into the luminescence reader instrument 44. The cassette 18 is removed from the luminescence reader instrument 44 by another robotic arm 52, which places the cassette 18 into a second storage compartment 54.

The luminescence reader instrument 44 is an optical-mechanical device designed as a modification of light optical-based, integrated circuit inspection stations used to "screen" integrated circuit "chips" for defects. Systems integrating environmental control, micro-robotics and optical readers are produced by companies such as Carl Zeiss [Jena, GmbH]. In addition to facilitating robotic handling, fluid delivery, and fast and precise scanning, two reading modes, high content and high throughput are supported. High-content readout is essentially the same as that performed by the ArrayScan reader (U.S. application Ser. No. 08/810983). In the high content mode, each location on the non-uniform micro-patterned array of cells is imaged at magnifications of 5–40× or more, recording a sufficient number of fields to achieve the desired statistical resolution of the measurement(s).

In the high throughput mode, the luminescence reader instrument 44 images the non-uniform micro-patterned array of cells at a much lower magnification of 0.2× to 1.0× magnification, providing decreased resolution, but allowing all the wells on the non-uniform micro-patterned array of cells to be recorded with a single image. In one embodiment, a 20 mm×30 mm non-uniform micro-patterned array of cells imaged at 0.5× magnification would fill a 1000×1500 array of 10 um pixels, yielding 20 um/pixel resolution, insufficient to define intracellular luminescence distributions, but sufficient to record an average response in a single well, and to count the numbers of a particular cell subtype in a well. Since typical integration times are on the order of seconds, the high throughput mode of reading technology, coupled with automated loading and handling, allows for the screening hundreds of compounds a minute.

Figure 13:
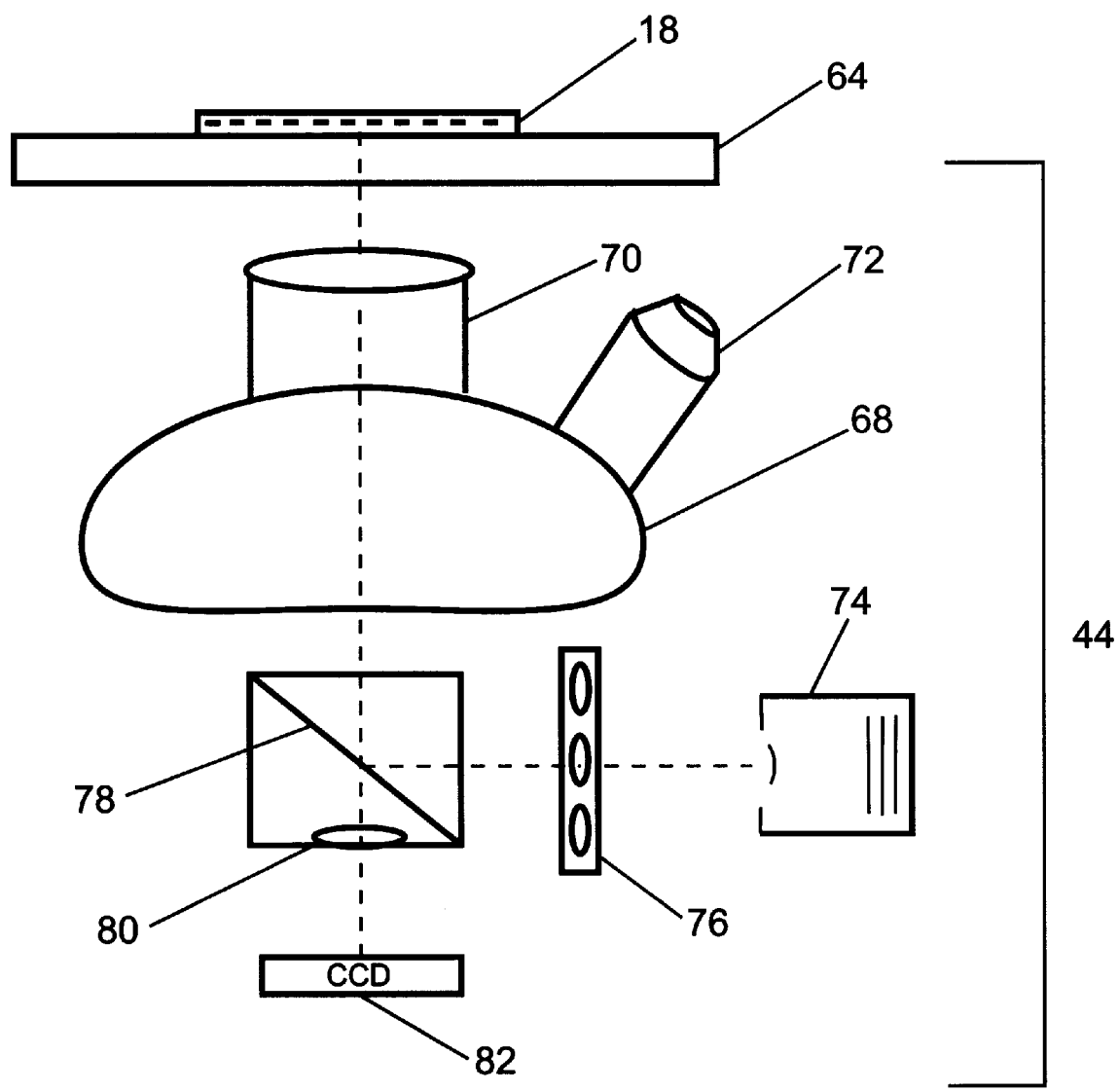
FIG. 13 is a diagram of one embodiment of the luminescence reader instrument optical system.

In one embodiment shown in FIG. 13, the luminescence reader instrument comprises an optical-mechanical design that is either an upright or inverted fluorescence microscope 44, which comprises a computer-controlled x,y,z-stage 64, a computer-controlled rotating nosepiece 68 holding a low magnification objective 70 (e.g., 0.5×) and one or more higher magnification objectives 72, a white light source lamp 74 with excitation filter wheel 76, a dichroic filter system 78 with emission filters 80, and a detector 82 (e.g., cooled charge-coupled device). For the high throughput mode, the low magnification objective 70 is moved into place and one or more luminescence images of the entire non-uniform micro-patterned array of cells is recorded.

Wells that exhibit some selected luminescence response are identified and further analyzed via high content screening, wherein the nosepiece 68 is rotated to select a higher magnification objective 72 and the x,y,z-stage 64 is adjusted to center the "selected" well for both cellular and subcellular high content screening, as described in U.S. application Ser. No. 08/810983.

In an alternate embodiment, the luminescence reader instrument 44 can utilize a scanned laser beam in either confocal or standard illumination mode. Spectral selection is based on multiple laser lines or a group of separate laser diodes, as manufactured by Carl Zeiss (Jena, GmbH, Germany) or as discussed in Denk, et al. (Science 248:73, 1990).

Another embodiment of the high throughput screening mode involves the use of a low-resolution system consisting of an array (1×8, 1×12, etc.) of luminescence exciters and luminescence emission detectors that scans subsets of the wells on a non-uniform micro-patterned array of cells. In a preferred embodiment, this system consists of bundled optical fibers, but any system that directs luminescence excitation light and collects luminescence emission light from the same well will suffice. Scanning the entire non-uniform micro-patterned array of cells with this system yields the total luminescence from each well, both from cells and the solution they are bathed in. This embodiment allows for the collection of luminescence signals from cell-free systems, so-called "homogeneous" assays.

Figure 14A:
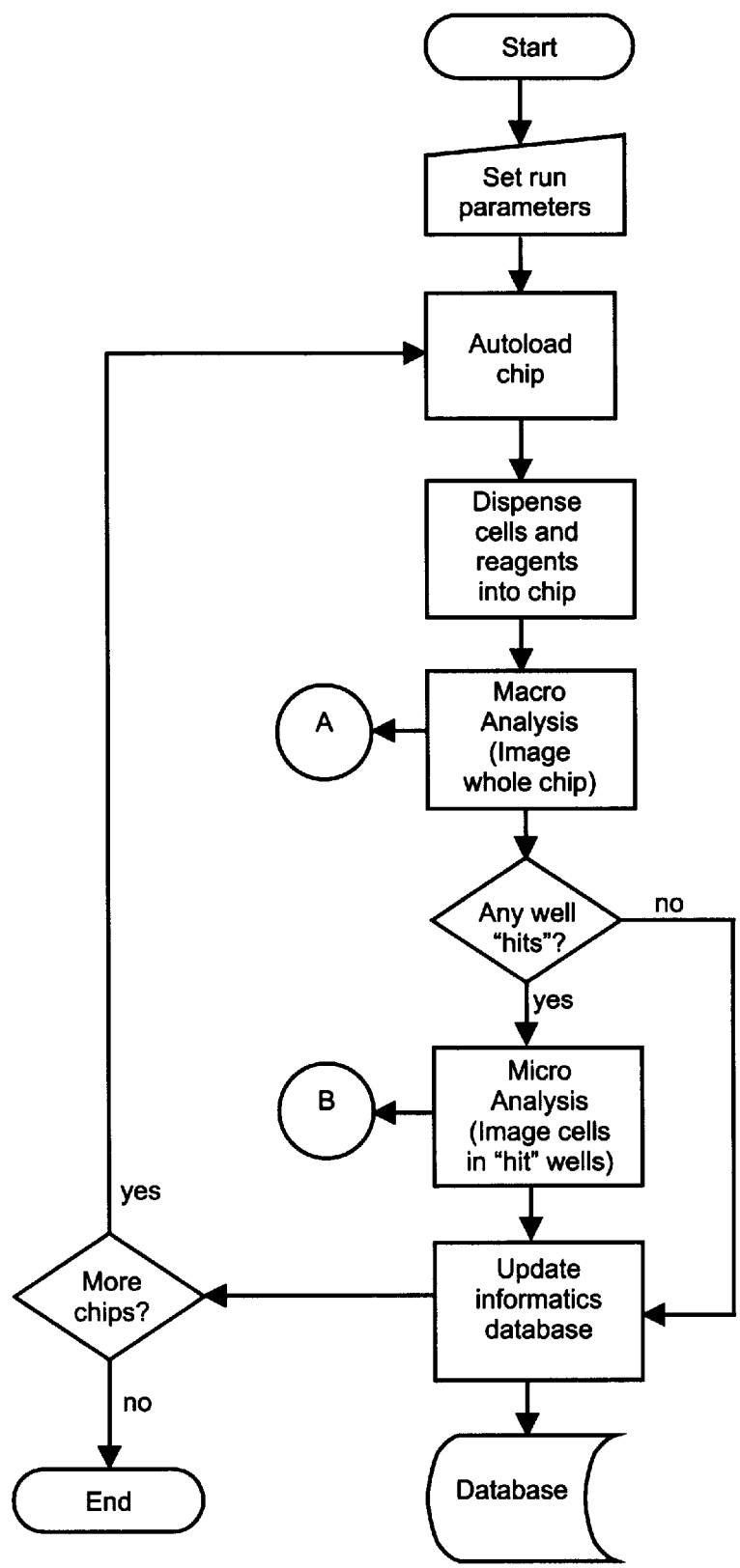
FIG. 14A is a flow chart providing an overview of the cell screening method.
Figure 14B:
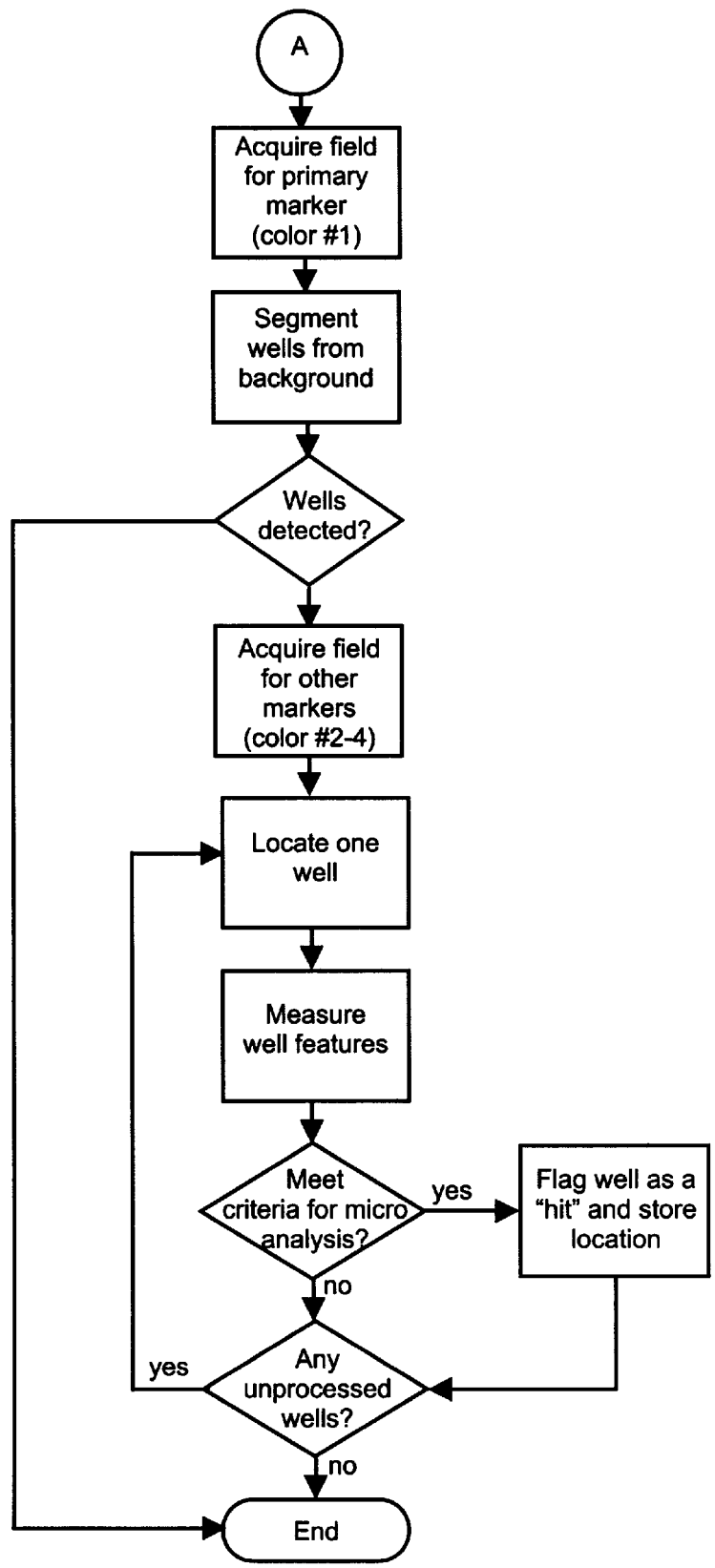
FIG. 14B is a Macro (High Throughput Mode) Processing flow chart.
Figure 14C:
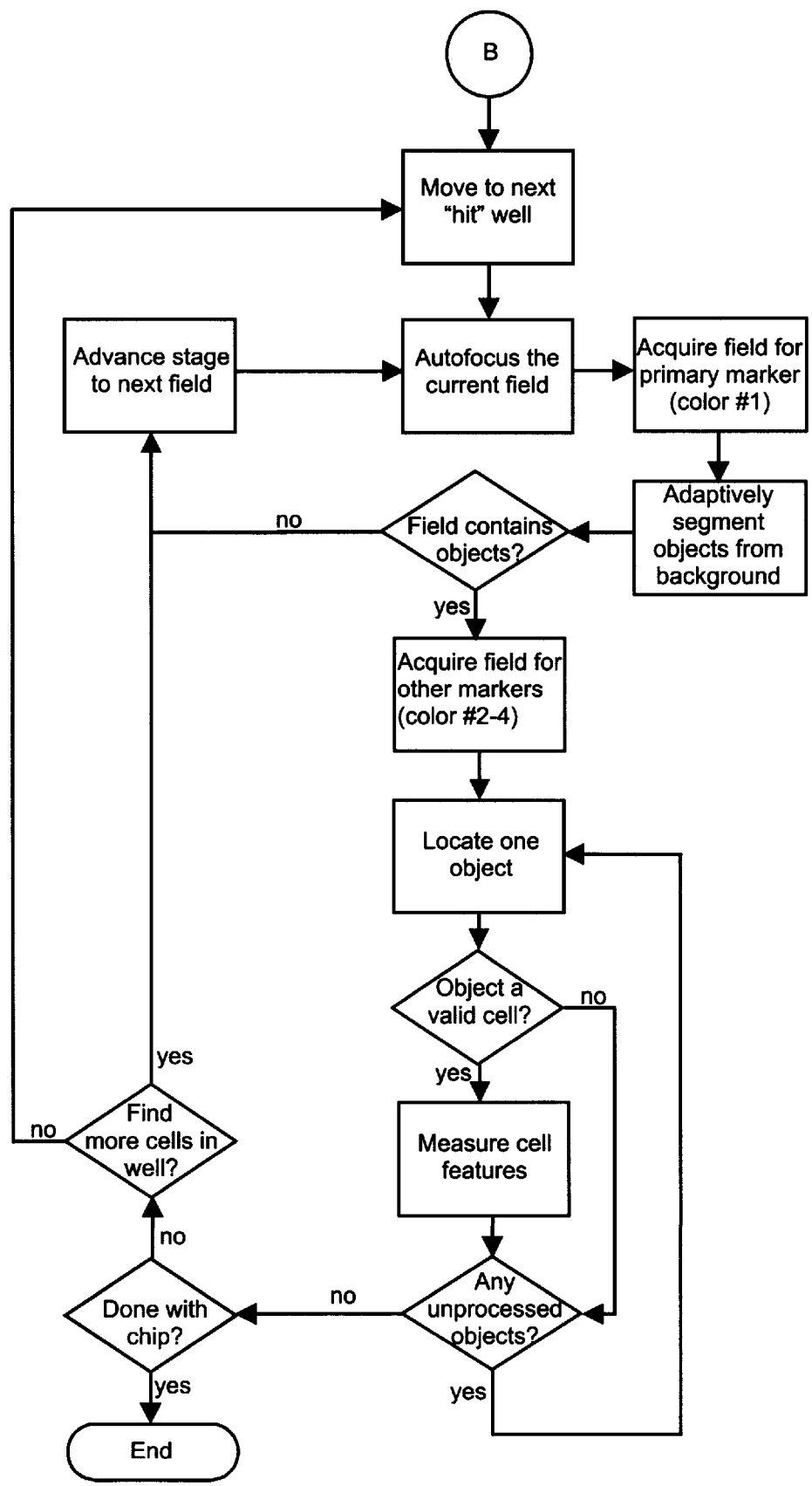
FIG. 14C is a Micro (High Content Mode) Processing flow chart.

FIG. 14A shows an algorithm, in the form of a flow chart, for analyzing a non-uniform micro-patterned array of cells in both the high throughput and high content modes using the luminescence reader instrument, which first uses high throughput detection to measure a response from the entire array "A". (FIG. 14B). Any well that responds above a preset threshold is considered a hit and the cells in that well are measured via high content screening. (FIG. 14C). The high content mode ("B") may or may not measure the same cell parameter measured during the high throughput mode ("A").

In another aspect of the invention, a cell screening system is disclosed, wherein the term "screening system" comprises the integration of a luminescence reader instrument, a cassette that can be inserted into the luminescent reader instrument comprising a non-uniform micro-patterned array of cells wherein the cells contain at least one luminescent reporter molecule and a chamber associated with the non-uniform micro-patterned array of cells, a digital detector for receiving data from the luminescence reader instrument, and a computer means for receiving and processing digital data from the digital detector.

Preferred embodiments of the luminescence reader instrument, and the cassette comprising the non-uniform micro-patterned array of cells and the chamber are disclosed above. A preferred embodiment of the digital detector is disclosed in U.S. application Ser. No. 08/810983, and comprises a high resolution digital camera that acquires luminescence data from the luminescence reader instrument and converts it to digital data. In a preferred embodiment, the computer means comprises a digital cable that transports the digital signals from the digital detector to the computer, a display for user interaction and display of assay results, a means for processing assay results, and a digital storage media for data storage and archiving, as described in U.S. application Ser. No. 08/810983.

Figure 15:
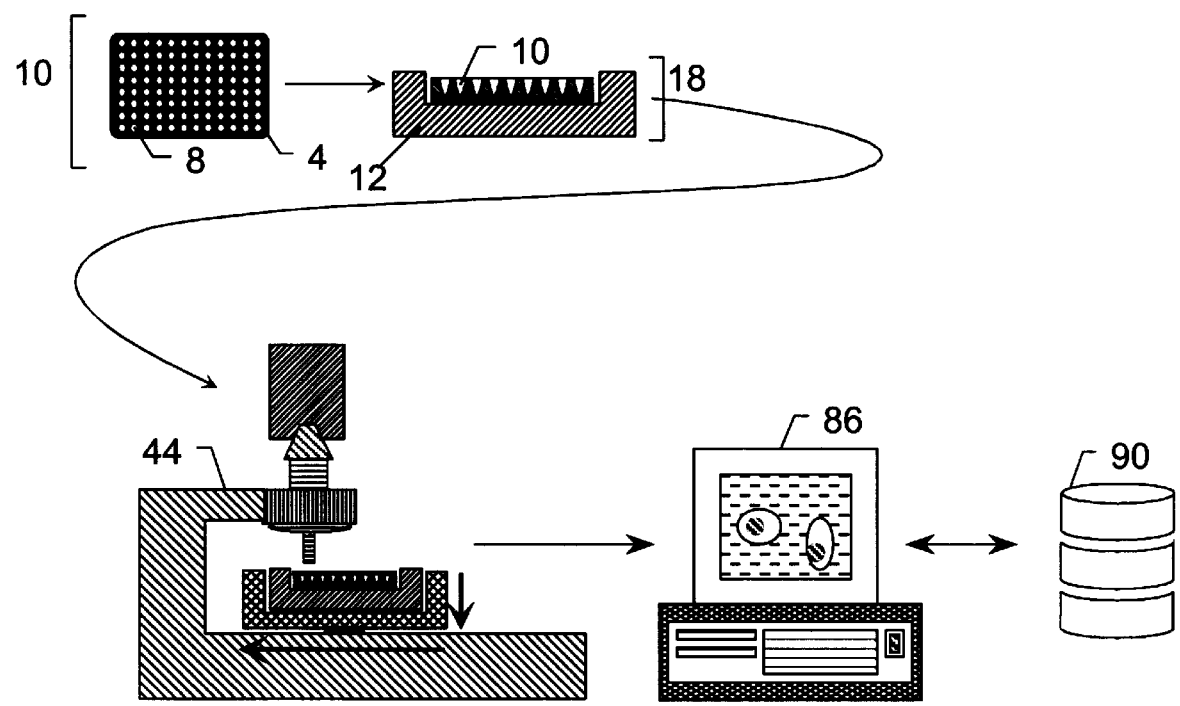
FIG. 15 is a diagram of the integrated cell screening system.
Figure 16:
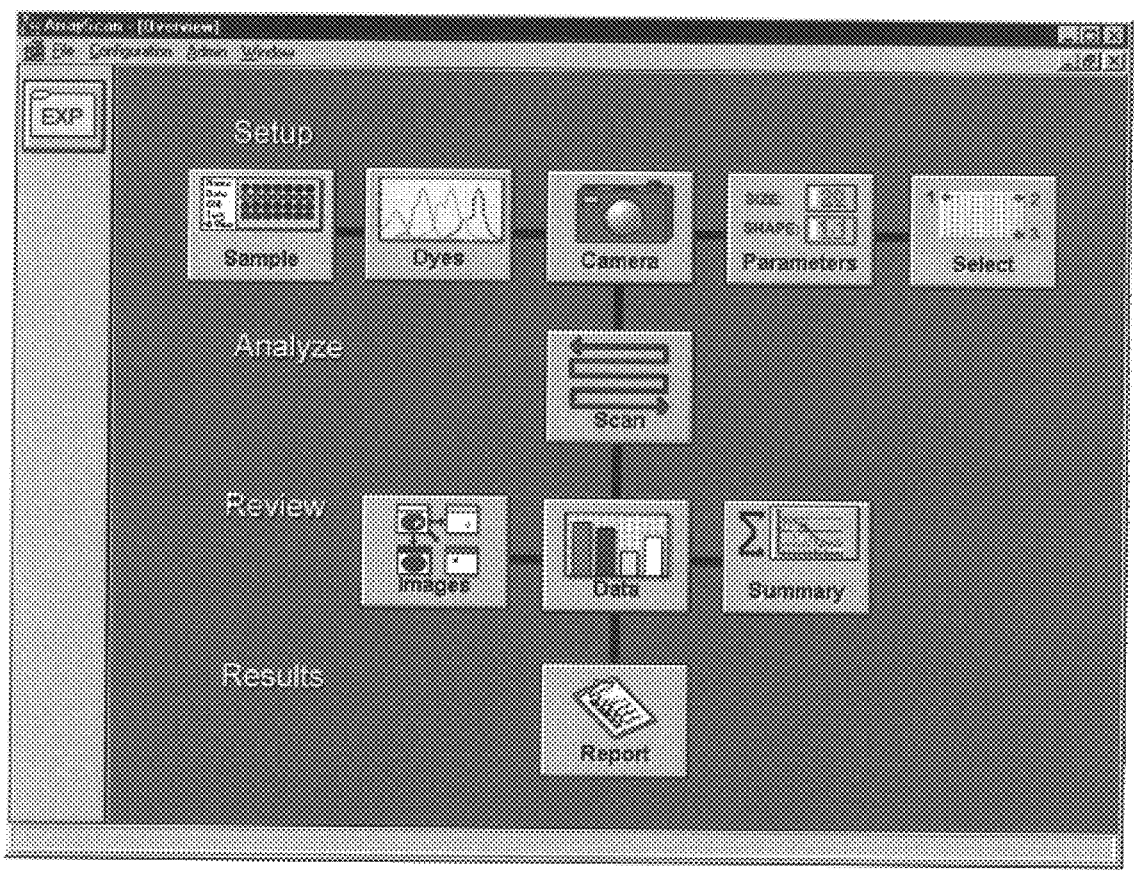
FIG. 16 is a photograph of the user interface of the luminescence reader instrument.

In a preferred embodiment, the cell screening system of the present invention comprises integration of the preferred embodiments of the elements disclosed above (FIG. 15). The non-uniform micro-patterned array of cells 10 comprises cells bound to micro-patterned chemical arrays in wells 8 on a base 4. The chamber 12 serves as a microfluidic delivery system for the addition of compounds to the non-uniform micro-patterned array of cells 10, and the combination of the two comprises the cassette 18. The cassette 18 is placed in a luminescence reader instrument 44. Digital data are processed as described above and in U.S. application Ser. No. 08/810983, hereby incorporated by reference in its entirety. The data can be displayed on a computer screen 86 and made part of a bioinformatics data base 90, as described in U.S. application Ser. No. 08/810983. This data base 90 permits storage and retrieval of data obtained through the methods of the invention, and also permits acquisition and storage of data relating to previous experiments with the cells. An example of the computer display screen is shown in FIG. 16.

The present invention may be better understood with reference to the accompanying Examples that are intended for purposes of illustration only and should not be construed to limit the scope of the invention, as defined in the claims appended hereto.

EXAMPLE 1

Coupling of Antibodies to Non-unizform Micro-patternied Array of Cells for the Attachment of Specific Lymphoid Cells 1. The cell line used was a mouse B cell lymphoma line (A20) that does not express IgM on its surface. A non-uniform micro-patterned array of cells was prepared for derivatization by being immersed overnight in 20% sulfuric acid, washed 2–3 times in excess distilled water, rinsed in 0.1M sodium hydroxide and blotted dry. The non-uniform micro-patterned array of cells was either used immediately or placed in a clean glass beaker and covered with parafilm for future use.

2. The non-uniform micro-patterned array of cells was placed in a 60 mm petri dish, and 3-Aminopropyltrimethoxysilane was layered onto the non-uniform micro-patterned array of cells ensuring complete coverage without running over the edges (approximately 0.2 ml for a 22×22 mm non-uniform micro-patterned array of cells, and approximately 0.5 ml for a 22×40 mm non-uniform micro-patterned array of cells). After 4 minutes at room temperature, the non-uniform micro-patterned array of cells was washed in deionized water and excess water was removed by blotting.

3. The non-uniform micro-patterned array of cells was placed in clean 60 mm petri dishes and incubated with glutaraldehyde (2.5% in PBS, approximately 2.5 ml) for 30 minutes at room temperature, followed by three PBS washes. Excess PBS was removed by blotting.

4. Cell nuclei in the non-uniform micro-patterned array of cells were labeled with a luminescent Hoechst dye during the blocking step. The appropriate number of lymphoid cells (see below) in C-DMEM were transferred to a 15 ml conical tube, and Hoechst dye was added to a final concentration of 10 $\mu$g/ml. Cells were incubated for 10–20 minutes at 37° C. in 5% $CO_2$, and then pelleted by centrifugation at 1000× g for 7 minutes at room temperature. The supernatant containing unbound Hoechst dye was removed and fresh media (C-DMEM) was added to resuspend the cells as follows: approximately 1.25–1.5×$10^5$ cells in 0.2 ml per 22×22 mm non-uniform micro-patterned array of cells, and approximately 2.5×$10^5$ cells in 0.75 ml for the 22×40 mm non-uniform micro-patterned array of cells.

5. The non-uniform micro-patterned array of cells was washed briefly in PBS and transferred to a clean, dry 60 mm petri dish, without touching the sides of the dish. Cells were carefully pipeted onto the top of the non-uniform micro-patterned array of cells at the density noted above. Dishes were incubated at 37° C. in 5% $CO_2$ for 1 hour. Unbound cells were then removed by repeated PBS washings.

6. Antibody solutions (Goat Anti-Mouse IgM or Goat Anti-Mouse Whole Serum) were spotted onto parafilm (50 μl for 22×22 mm non-uniform micro-patterned array of cells, 100 μl for a 22×40 mm non-uniform micro-patterned array of cells). The non-uniform micro-patterned array of cells was inverted onto the spots, so that the antiserum covered the entire surface of the treated non-uniform micro-patterned array of cells without trapping air bubbles. The non-uniform micro-patterned array of cells was incubated with the antibody solution for 1 hour at room temperature.

7. The non-uniform micro-patterned array of cells was carefully lifted from the parafilm, placed in a clean 60 mm petri dish, and washed three times with PBS. Unreacted sites are then blocked by the addition of 2.5 ml of 10% serum (calf or fetal calf serum in DMEM or Hank's Balanced Salt Solution) for 1 hour at room temperature.

Figure 17:
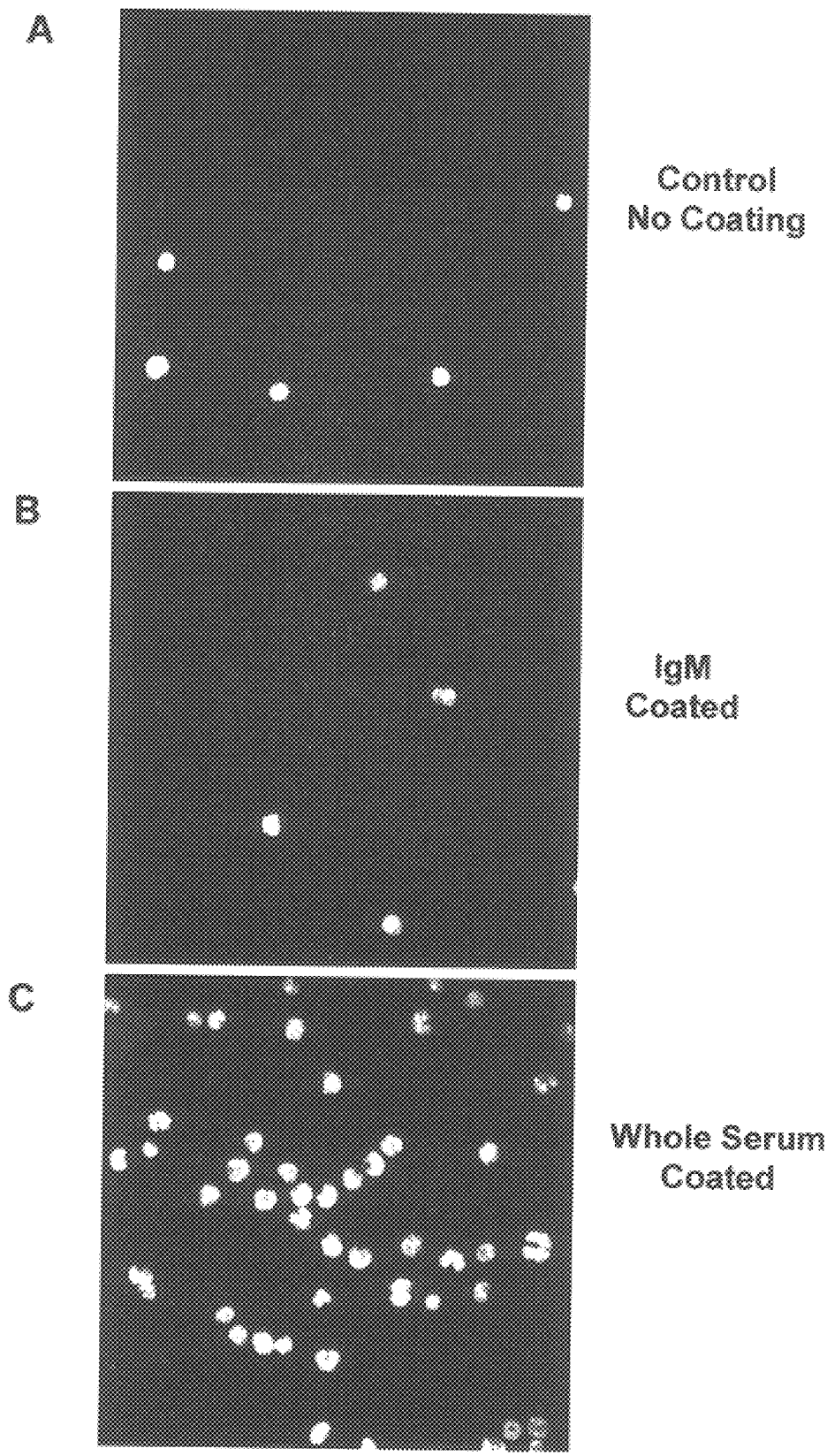
FIG. 17A is a photograph showing lymphoid cells non-specifically attached to an unmodified substrate.
FIG. 17B is a photograph showing lymphoid cells non-specifically attached to an IgM-coated substrate.
FIG. 17C is a photograph showing lymphoid cells specifically bound to a whole anti-serum-coated substrate.

8. Both cell lines should bind to the anti-mouse whole serum, but only the X16s should bind to the anti-mouse IgM. The binding of specific lymphoid cell strains to the chemically modified surface is shown in FIG. 17. The mouse lymphoid A20 cell line, lacking surface IgM molecules but displaying IgG molecules, bound much more strongly to the surface modified with whole goat anti-mouse serum (FIG. 17C) than to the surface modified with goat anti-mouse IgM (FIG. 17B) or an uncoated slide (FIG. 17A).

EXAMPLE 2

High-Content and High Throughput Screen.

The insulin-dependent stimulation of glucose uptake into cells such as adipocytes and myocytes requires a complex orchestration of cytoplasmic processes that result in the translocation of GLUT4 glucose transporters from an intracellular compartment to the plasma membrane. A number of molecular events are triggered by insulin binding to its receptor, including direct signal transduction events and indirect processes such as the cytoskeletal reorganizations required for the translocation process. Because the actin-cytoskeleton plays an important role in cytoplasmic organization, intracellular signaling ions and molecules that regulate this living gel can also be considered as intermediates of GLUT4 translocation.

A two level screen for insulin mimetics is implemented as follows. Cells carrying a stable chimera of GLUT4 with a Blue Fluorescent Protein (BFP) are arranged on the non-uniform micro-patterned array of cells arrays, and then loaded with the acetoxymethylester form of Fluo-3, a calcium indicator (green fluorescence). The array of locations are then simultaneously treated with an array of compounds using the microfluidic delivery system, and a short sequence of Fluo-3 images of the whole non-uniform micro-patterned array of cells are analyzed for wells exhibiting a calcium response in the high throughput mode. The wells containing compounds that induced a response, are then analyzed on a cell by cell basis for evidence of GLUT4 translocation to the plasma membrane (i.e., the high-content mode) using blue fluorescence detected in time and space.

Figure 19:
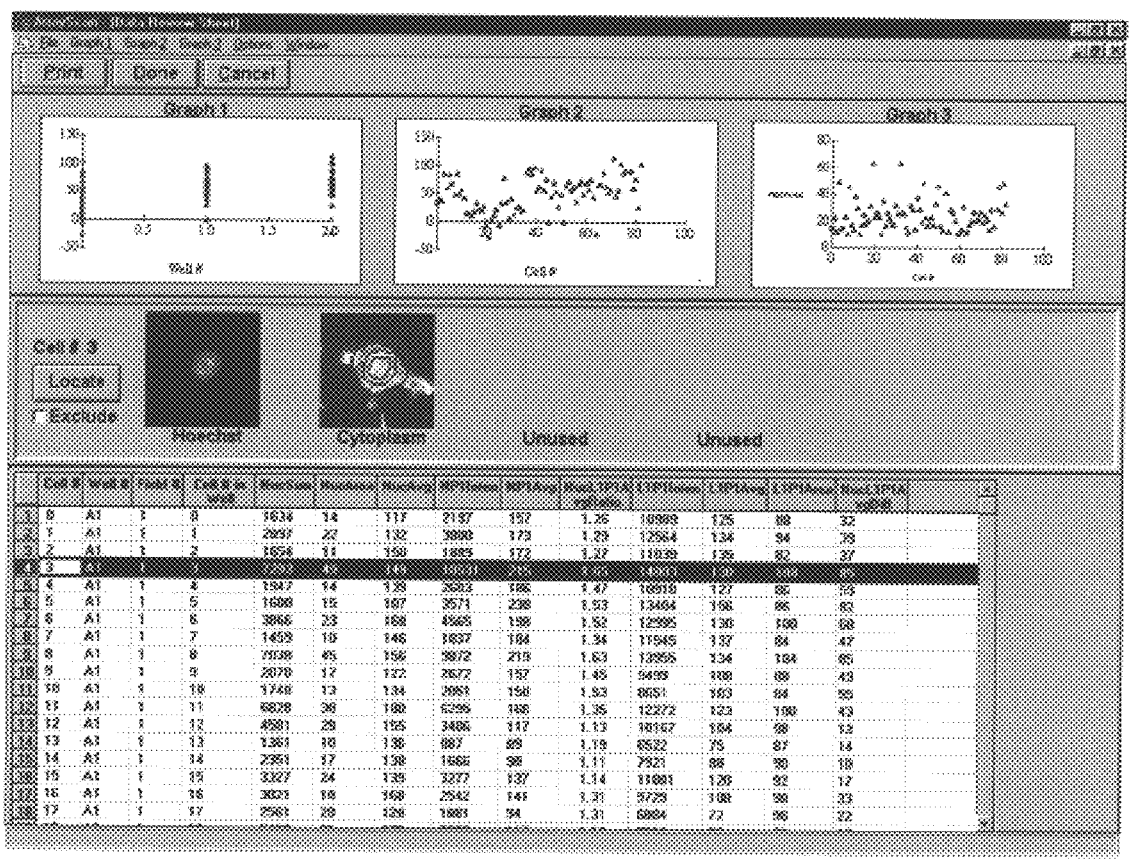
FIG. 19 is a photographic image showing the display of cell data gathered from the high content mode.

FIG. 18 depicts the sequential images of the whole non-uniform micro-patterned array of cells in the high throughput mode (FIG. 18A) and the high content mode (FIG. 18B). FIG. 19 shows the cell data from the high content mode.

What is claimed is:

1. A method for producing a cassette for cell screening, comprising:
    a) providing a base with a surface
    b) preparing a micro-patterned chemical array;
    c) modifying the micro-patterned chemical array to produce a modified micro-patterned chemical array comprising multiple different cell binding sites on the surface of the base, wherein the different cell binding sites interact with different cell types, wherein a cell binding site comprises a well;
    d) binding cells to the modified micro-patterned chemical array to produce an ordered array of cell types seeded on the wells; and
    e) providing a fluid delivery system for delivering a combinatorial of reagents to the ordered array of cell types; wherein said fluid delivery system comprises a chamber that mates with the base containing the ordered array of cell types, wherein the chamber comprises:
        (i) etched domains matching the wells on the surface of the base, and
        (ii) microfluidic channels that supply fluid to the etched domains.

2. The method of claim 1, further comprising providing microfluidic channels to remove excess fluid from the etched domains.

3. The method of claim 1, wherein a single microfluidic channel supplies fluid to a single etched domain, to provide separate fluid flow to each etched domain, and wherein the etched domains are larger in diameter than the wells of the ordered array of cell types.

4. The method of claim 1, further comprising providing a plug between the end of the microfluidic channel and the etched domain.

5. The method of claim 1, wherein a microfluidic channel extends from each etched domain to the edge of the chamber.

* * * * *